(12) United States Patent
Muzzio et al.

(10) Patent No.: US 11,344,494 B2
(45) Date of Patent: May 31, 2022

(54) FORMULATION AND MANUFACTURE OF PHARMACEUTICALS BY IMPREGNATION ONTO POROUS CARRIERS

(71) Applicant: Rutgers, The State University of New Jersey, New Brunswick, NJ (US)

(72) Inventors: Fernando J. Muzzio, Sparta, NJ (US); Benjamin J. Glasser, Princeton, NJ (US); Plamen I. Grigorov, Matawan, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 15/984,577

(22) Filed: May 21, 2018

(65) Prior Publication Data

US 2018/0263896 A1 Sep. 20, 2018

Related U.S. Application Data

(62) Division of application No. 13/817,448, filed as application No. PCT/US2011/048422 on Aug. 19, 2011, now Pat. No. 10,004,682.

(60) Provisional application No. 61/376,568, filed on Aug. 24, 2010.

(51) Int. Cl.
| | |
|---|---|
| *A61K 9/00* | (2006.01) |
| *A61K 9/16* | (2006.01) |
| *A61K 9/20* | (2006.01) |

(52) U.S. Cl.
CPC ............ *A61K 9/00* (2013.01); *A61K 9/0075* (2013.01); *A61K 9/1611* (2013.01); *A61K 9/1694* (2013.01); *A61K 9/2009* (2013.01)

(58) Field of Classification Search
CPC ...... A61K 9/0075; A61K 9/1611; A61K 9/00; A61K 9/2009; A61K 9/1694
See application file for complete search history.

(56) References Cited

U.S. PATENT DOCUMENTS

| | | | |
|---|---|---|---|
| 5,055,307 A | 10/1991 | Tsuru et al. | |
| 6,136,288 A | 10/2000 | Bauer et al. | |
| 7,569,274 B2 | 8/2009 | Besse et al. | |
| 2003/0017189 A1 | 1/2003 | Wong et al. | |
| 2008/0026057 A1* | 1/2008 | Benke ................. | A61K 9/2077 424/468 |
| 2009/0017125 A1 | 1/2009 | Lynenskjold et al. | |
| 2009/0162435 A1 | 6/2009 | Bunick et al. | |
| 2009/0202649 A1 | 8/2009 | Gore et al. | |
| 2009/0298847 A1 | 12/2009 | Jeon et al. | |
| 2010/0055133 A1 | 3/2010 | Duffield et al. | |
| 2011/0064805 A1* | 3/2011 | Obae ................... | A61K 9/2018 424/464 |
| 2013/0053446 A1 | 2/2013 | Muzzio et al. | |
| 2014/0378401 A1 | 12/2014 | Horn | |
| 2017/0157049 A1 | 6/2017 | Dandl et al. | |
| 2018/0263896 A1 | 9/2018 | Muzzio et al. | |
| 2019/0192946 A1 | 6/2019 | Demkowski et al. | |
| 2020/0024736 A1 | 1/2020 | Gangakhedkar et al. | |

FOREIGN PATENT DOCUMENTS

| | | |
|---|---|---|
| AU | 2009224418 A2 | 10/2010 |
| EP | 0266113 | 5/1988 |
| WO | 1997/047290 | 12/1997 |
| WO | 2004/022037 | 3/2004 |
| WO | 2005/034908 | 4/2005 |
| WO | 2007086646 A1 | 8/2007 |
| WO | 2008/014175 | 1/2008 |
| WO | 2009/113522 | 9/2009 |
| WO | 2009/135646 | 11/2009 |
| WO | 2010094471 A1 | 8/2010 |
| WO | 20130091006 A1 | 6/2013 |
| WO | 2015193485 A1 | 12/2015 |

OTHER PUBLICATIONS

European Extended Search Report dated Feb. 4, 2014, issued in European Application No. 11820429.6.
Kukkar, V. et al., "Mixing and forumulation of low dose drugs: underlying problems and solutions", Thai Journal of Pharmaceutical Sciences, Dec. 31, 2008, pp. 43-58.
International Search Report dated Jan. 11, 2012, in Application No. PCT/US2011/048422.
Nguyen et al., "Protein Powders for Encapsulation: A Comparision of Spray-Freeze Drying and Spray Drying of Darbepoetin Alfa.", Pharmaceutical Research, vol. 21, No. 3, Mar. 2004, p. 507.
Written Opinion dated Jan. 11, 2012, in Application No. PCT/US2011/048422.

* cited by examiner

*Primary Examiner* — Robert S Cabral
(74) *Attorney, Agent, or Firm* — Fox Rothschild LLP

(57) ABSTRACT

The present invention provides an impregnated porous carrier material comprising at least one active pharmaceutical ingredient (API) impregnated throughout the internal surface of a porous carrier. The present invention further provides immediate release and sustained release pharmaceutical dosage forms comprising the impregnated porous carrier material disclosed herein such that any single active pharmaceutical ingredient (API) content variability in the finished drug product has a relative standard deviation of less than 3%.

19 Claims, 22 Drawing Sheets

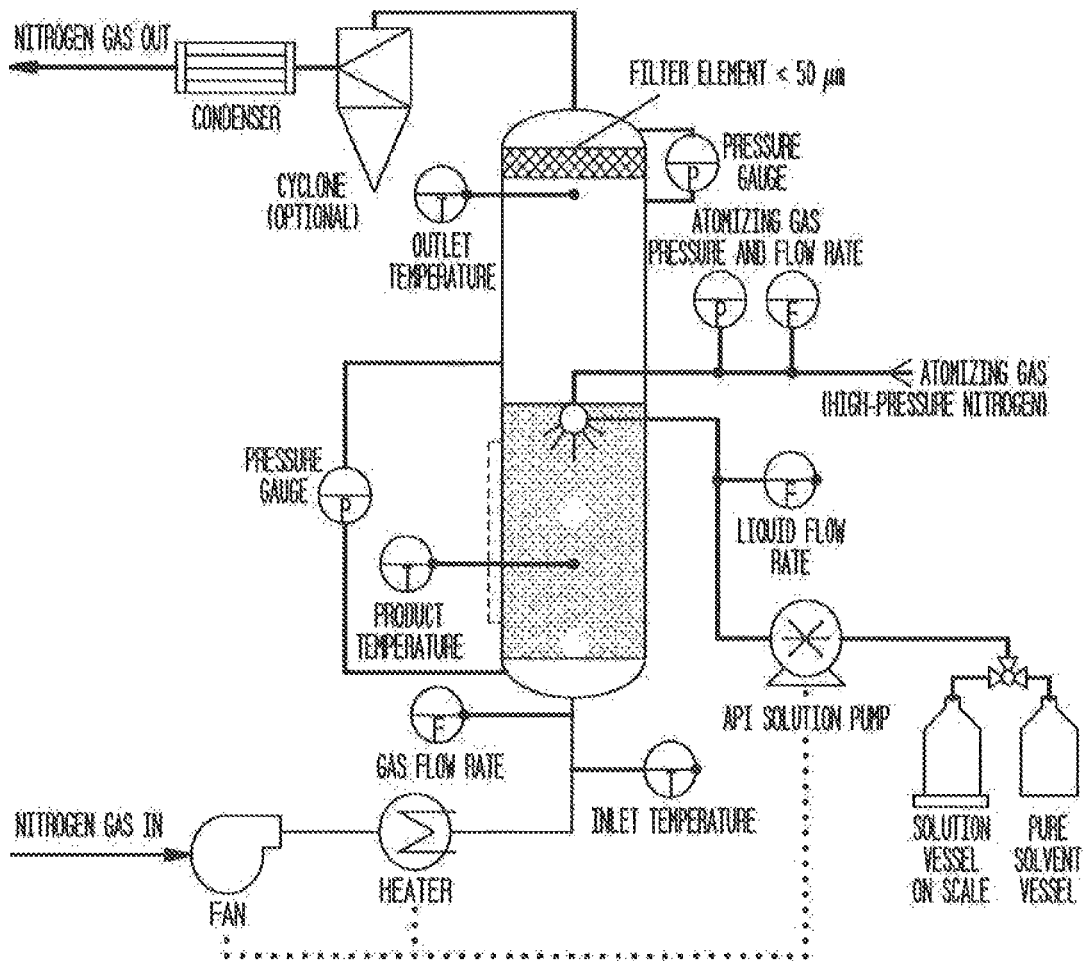
FIG. 1
FLUIDIZED BED IMPREGNATION SYSTEM

FIG. 2A
PHARMACEUTICAL EXCIPIENTS
ANHYDROUS CaHPO$_4$-EMCOMPRESS®
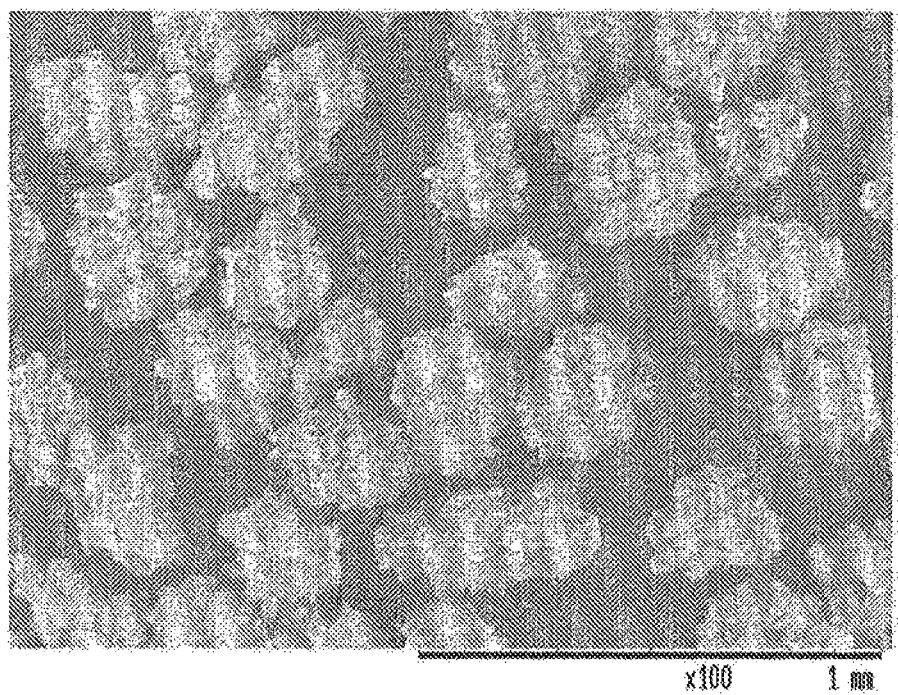
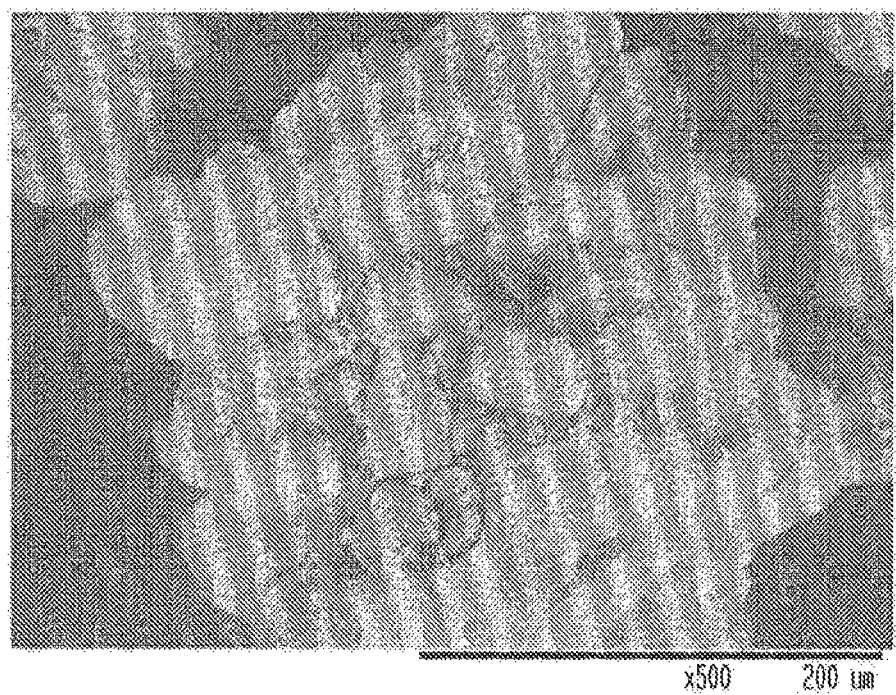

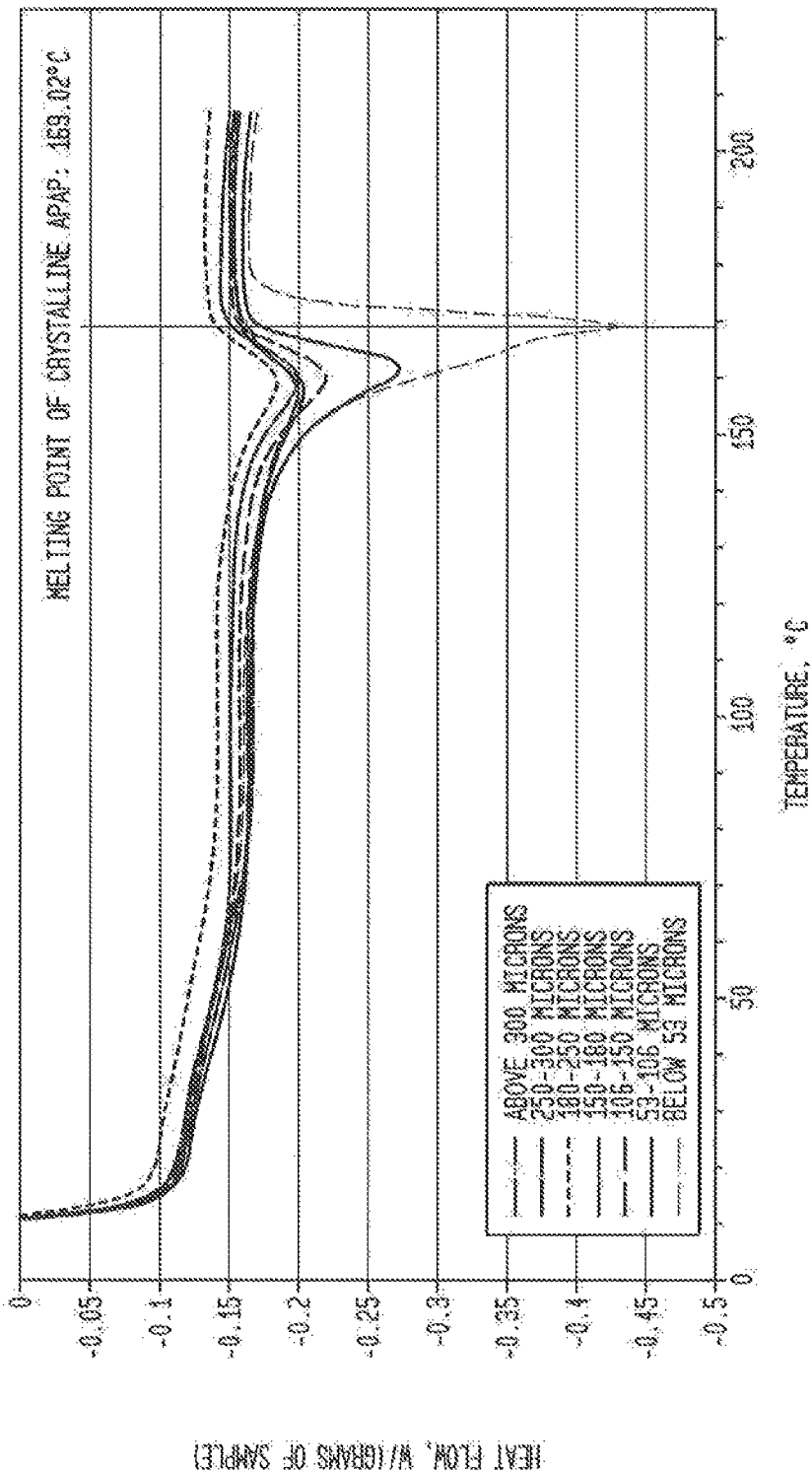

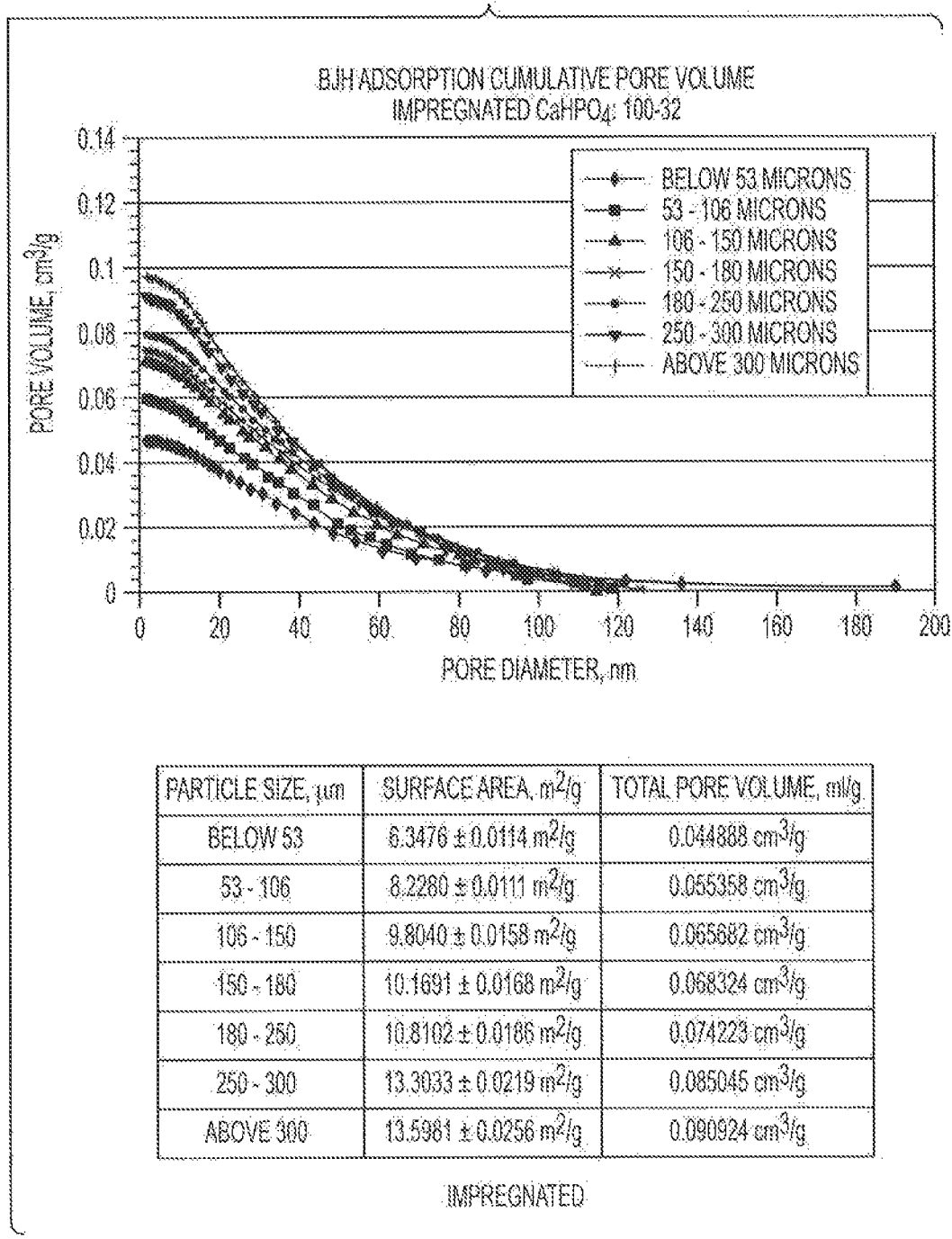

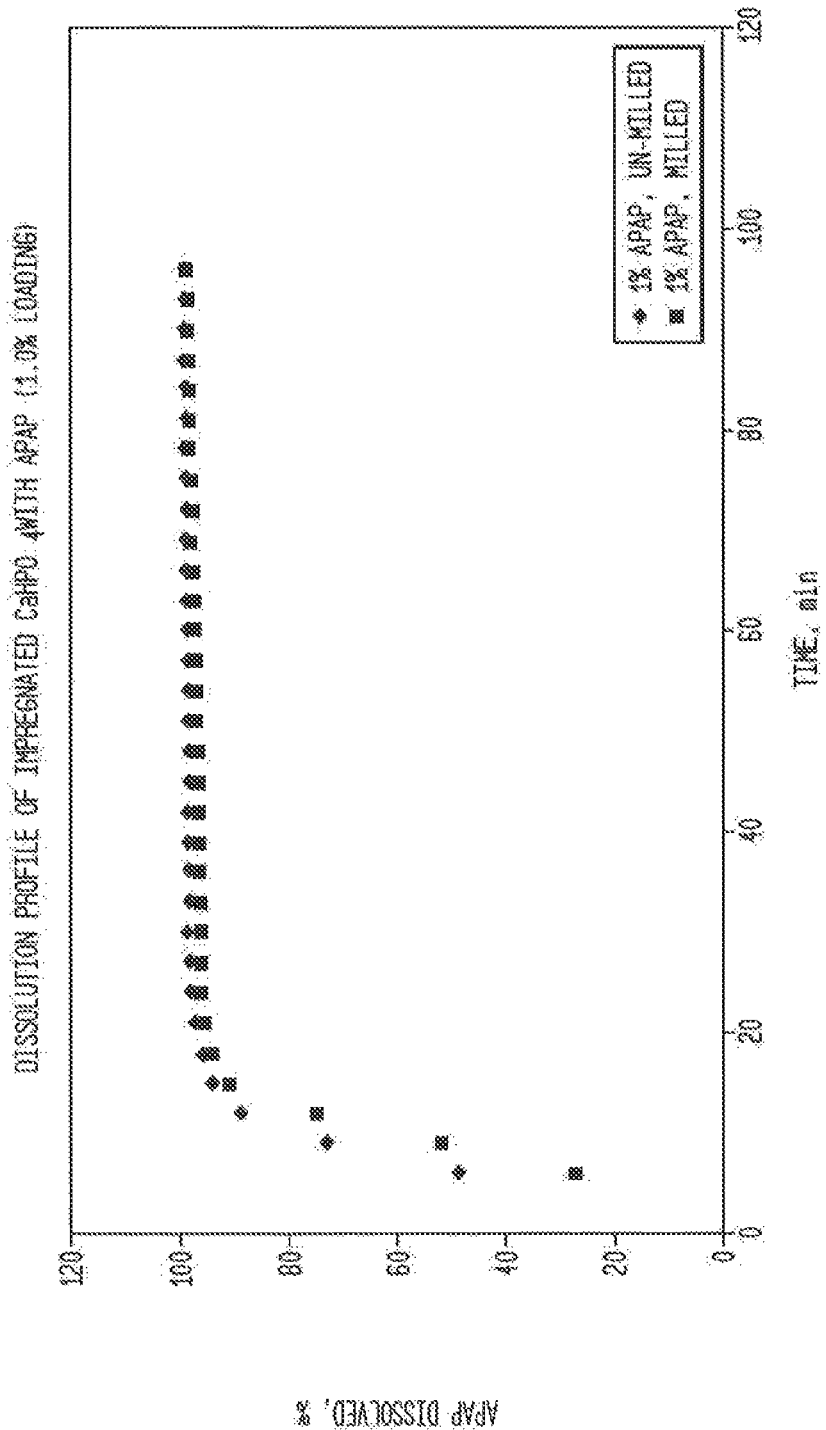

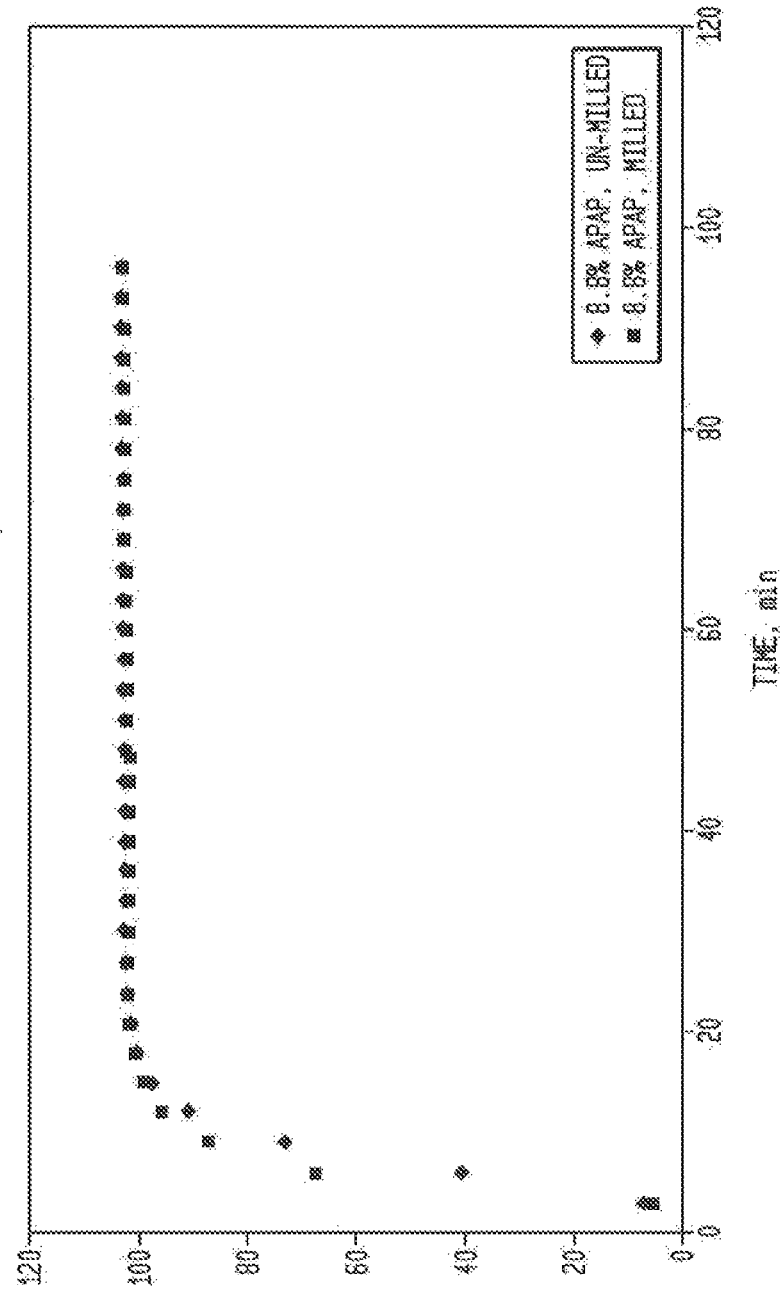

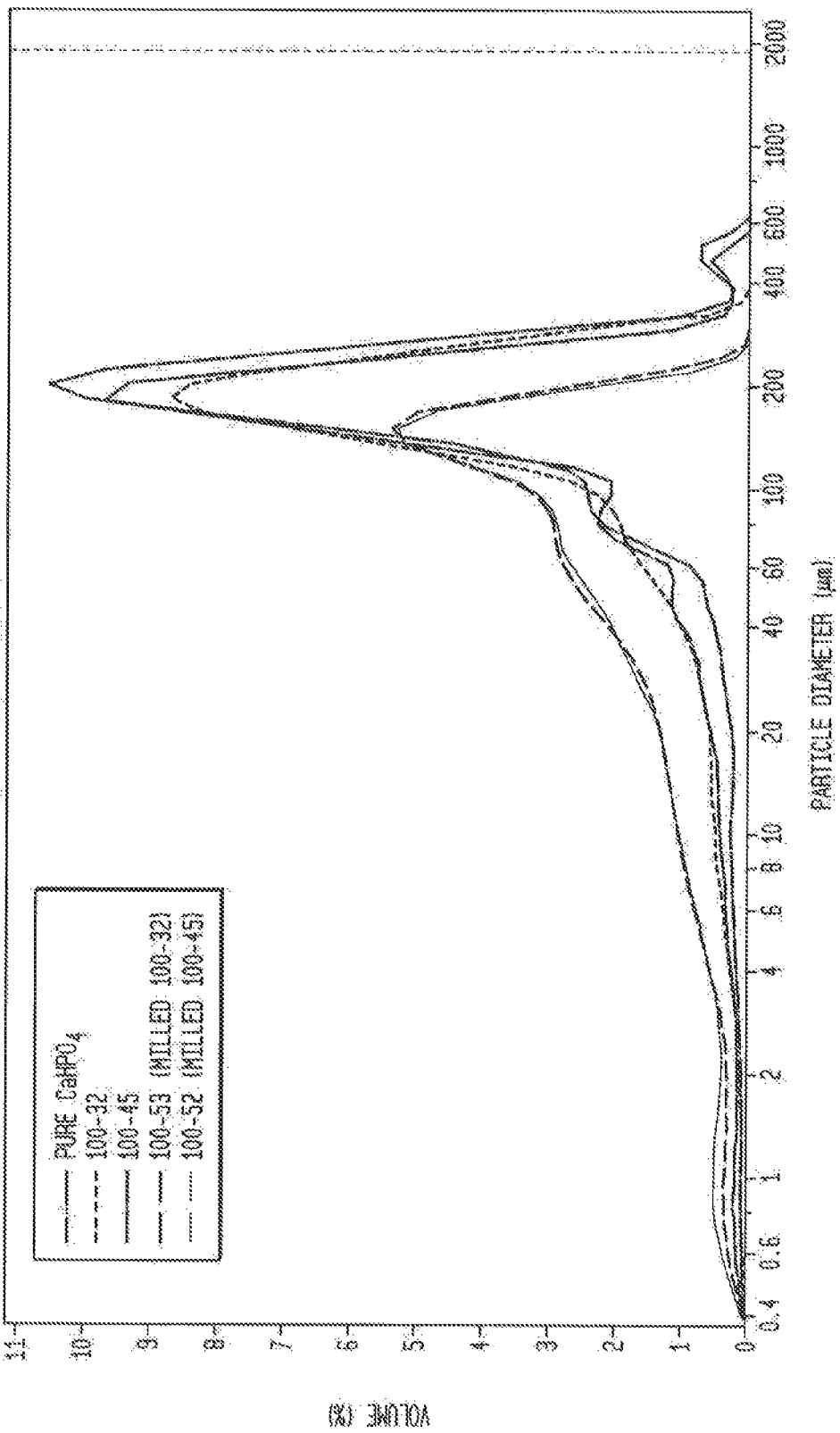

FIG. 9B

|  | $X_{10}$, μm | $X_{25}$, μm | $X_{50}$, μm | $X_{75}$, μm | $X_{90}$, μm |
|---|---|---|---|---|---|
| PURE CaHPO$_4$ | 48.82 | 112.7 | 176.0 | 221.8 | 264.5 |
| 0.70% | 19.17 | 72.86 | 150.0 | 199.9 | 241.7 |
| 1.00% | 18.05 | 75.57 | 155.6 | 202.1 | 241.6 |
| MILLED, 0.70% | 5.57 | 20.00 | 65.83 | 131.0 | 171.7 |
| MILLED, 1.00% | 3.88 | 17.50 | 60.84 | 126.0 | 165.9 |

FIG. 14

BLEND UNIFORMITY ON IMPREGNATED CaHPO$_4$ WITH IBUPROFEN

| BATCH | AVERAGE LOADING*, % (BY HPLC ANALYSIS) | % RSD |
|---|---|---|
| BATCH #1, UN-MILLED | 10.62 | 2.19 |
| BATCH #2, UN-MILLED | 10.48 | 2.38 |

*TARGET LOADING (SPRAYED-IN AMOUNT): 10.0%

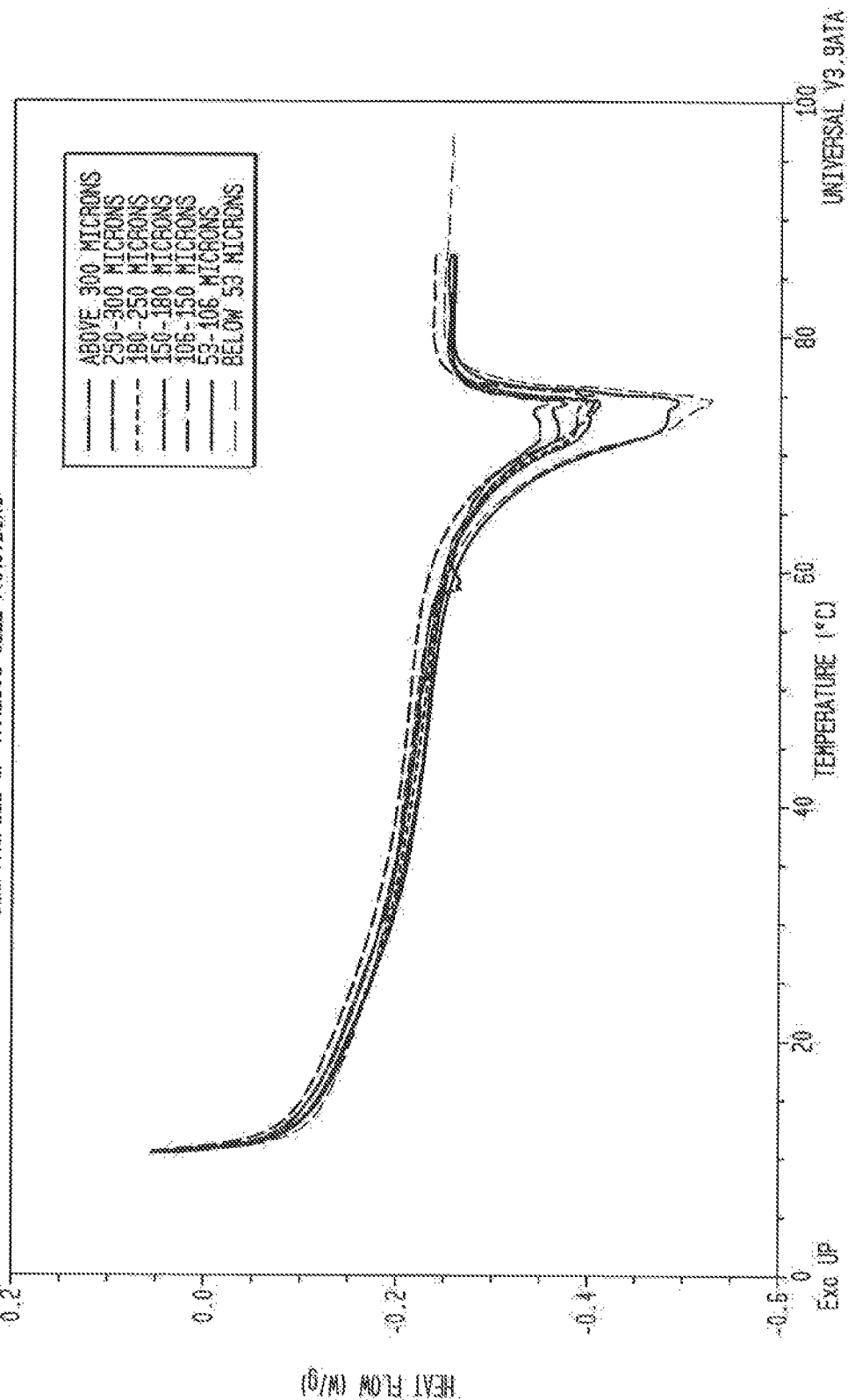

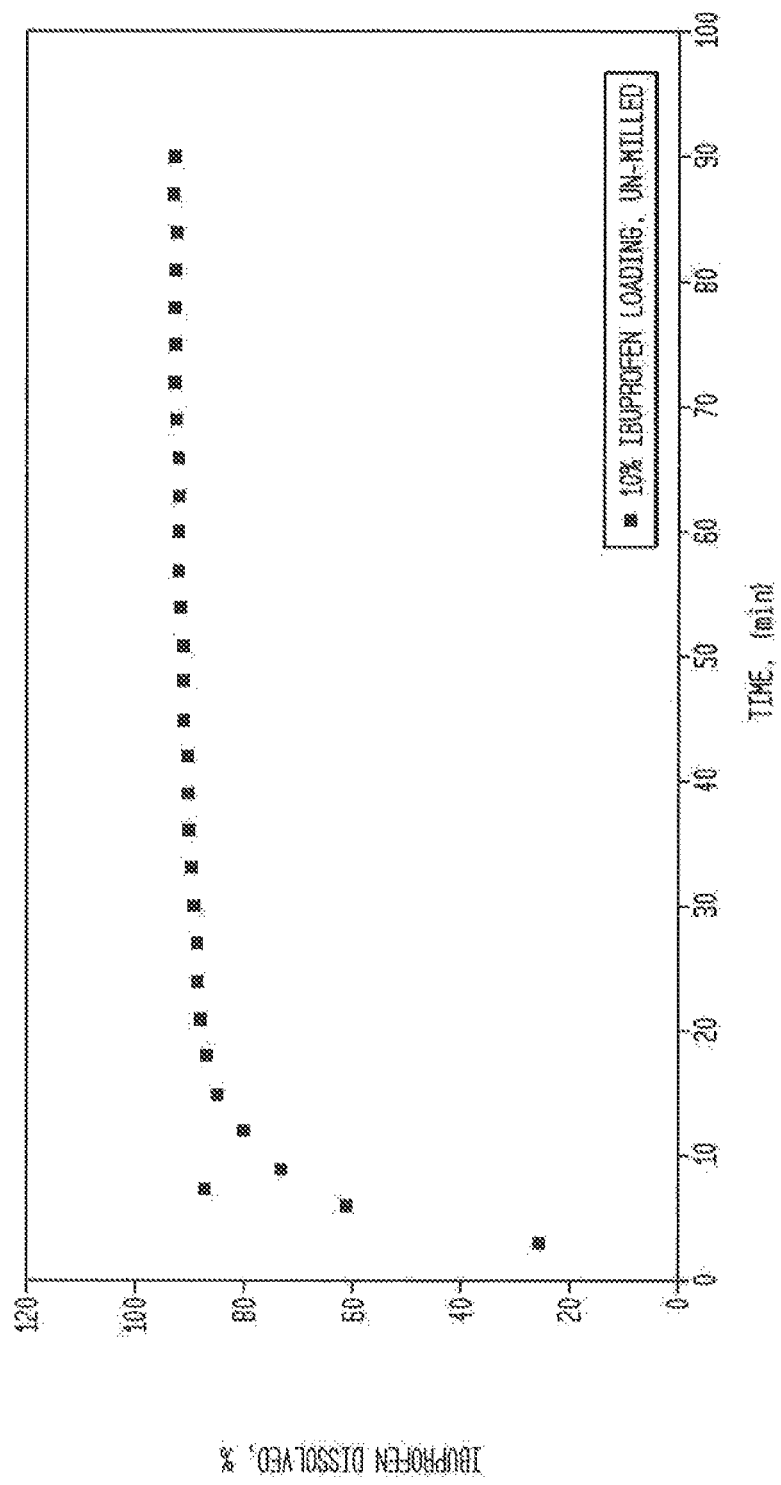

FORMULATION AND MANUFACTURE OF PHARMACEUTICALS BY IMPREGNATION ONTO POROUS CARRIERS

CROSS REFERENCE TO RELATED APPLICATIONS

This Divisional application claims the benefit of priority to U.S. Non-Provisional application Ser. No. 13/817,448 (filed May 28, 2013), which claims the benefit of priority to International Patent Application No. PCT/US2011/048422 (filed Aug. 19, 2011), which claims the benefit of priority to U.S. Provisional Application No. 61/376,568 (filed Aug. 24, 2010) entitled "FORMULATION AND MANUFACTURE OF PHARMACEUTICALS BY IMPREGNATION ONTO POROUS CARRIERS." The entire contents of each application are incorporated herein by reference.

FIELD OF THE INVENTION

The described invention relates to drug product development and manufacturing thereof.

BACKGROUND

Approximately 65% of all prescription drugs are manufactured as solid dosage forms, which include tablets and capsules. In both cases the final formulation consists of a carrier (or mixtures of carriers) and an active pharmaceutical ingredient ("API") which is homogeneously distributed throughout the carrier. For very potent drugs the amount of API in the solid dosage form can be as low as 0.1% by weight. This very low API loading poses one of the biggest problems in pharmaceutical product development: the control of blend uniformity. Low API content variability in the blend or high blend homogeneity are highly desired and strictly enforced by the U.S. Food and Drug Administration ("FDA"). Current guidelines developed by the FDA require API content variability in finished drug products to have relative standard deviation ("RSD") of no higher than 6%, with lower being better. In the commonly available approaches for blend uniformity control (for example, direct blending, wet or dry granulation) as the API concentration decreases, the variability of the blend increases; this makes it very difficult to meet FDA's requirements for low drug loadings. Therefore, a process or method that is able to tightly control API variability in blends, regardless of drug loadings, has become very desirable.

Another important aspect of pharmaceutical process development is the final cost. As pharmaceutical companies strive to develop cheaper and more affordable drugs, any possible elimination of lengthy and expensive unit operations will become commercially advantageous. One group of such unit operations is associated with the control of API attributes (size, size distribution, shape, crystal form, bulk density, etc.). These unit operations can include crystallization and various milling and de-lumping steps. The need for control of API attributes is solely dictated by the drug product development and usually is associated with improvements in blend uniformity, drug release profile, and physical stability of the finished product. Having a formulation process that can make these and other steps unnecessary will provide a large advantage to pharmaceutical companies and the industry as a whole.

In addition to cost savings in the manufacturing process, a very important part in the overall economics is the cost associated with research and development efforts. Currently, to at least some degree, these research investments are driven by the difficulty of the particular drug formulation. This generally is true for new molecules, where processing difficulties can cause delays in launching the product, and for generic products, where difficulties in developing a suitable formulation often are the paramount factor controlling successful development. These difficulties can be associated with the API properties (difficult to control crystal form, low bulk density, cohesive powders, difficult to achieve particle size distribution ("PSD"), etc.) or with the drug product properties (low blend uniformity, inconsistent release profile, poor powder flow, etc.). There is interest in having a robust manufacturing process that can be applied to a number of products regardless of the individual API properties and specifics. One area that can greatly benefit from such a robust manufacturing platform is the preparation of clinical supplies, whether for early phase studies for new molecules, or for bioequivalence studies for generic versions of existing products. The uncertainty of the drug's future at that stage makes such a platform extremely cost effective and highly desirable for pharmaceutical companies.

The described invention addresses these problems. The described invention provides a method for impregnating a drug solution throughout the volume of a porous carrier by spraying the solution onto the carrier in a fluid bed processor, generating a composite particle in which API bulk properties are no longer important.

SUMMARY

According to one aspect, the described invention provides a method for distributing at least one active pharmaceutical ingredient (API) across a volume of a preformed porous carrier via impregnation, the method comprising: (a) dissolving at least one active pharmaceutical ingredient (API) in a solvent to form an active pharmaceutical ingredient (API) solution; (b) contacting a porous carrier with the at least one active pharmaceutical ingredient (API) of (a) in a contactor to form an active pharmaceutical ingredient (API) impregnated porous carrier; and (c) drying the at least one active pharmaceutical ingredient (API) impregnated porous carrier.

According to one embodiment of the method, the method can achieve a substantially uniform distribution of one or more APIs across the volume of a preformed porous support such that any single API content variability in a finished drug product has a relative standard deviation of less than 3%. According to another embodiment, the contacting step (b) and drying step (c) takes place in a fluidized bed. According to another embodiment, the active pharmaceutical ingredient (API) impregnated porous carrier is dried in a contactor during step (b). According to another embodiment, the contactor comprises an agitated vessel, a tumbler, and a tray oven. According to another embodiment, contacting step (b) comprises spraying. According to another embodiment, the at least one pharmaceutical ingredient comprises acetaminophen, ibuprofen, indometacin/indomethacin, flufenamic acid, Imatinib, flufenamic acid, erlotinib hydrochloride, vitamin D, a steroid, estrodial, or a combination thereof. According to another embodiment, the preformed porous carrier is of a high porosity of 20% to 80% pores by volume. According to another embodiment, the porous carrier is a pharmaceutical carrier. According to another embodiment, the porous carrier is $CaHPO_4$. According to another embodiment, the porous carrier is anhydrous $CaHPO_4$. According to another embodiment, the active pharmaceutical ingredient (API) impregnated porous carrier is a blend. According to another embodiment, the porous carrier is impregnated in a contactor comprising a fluidized bed, a stirred vessel, and a tumbler. According to another embodiment, the method further comprises preparing a final dosage form for making a substantially uniform pharmaceutical product containing the at least one active pharmaceutical ingredient (API) impregnated porous carrier, wherein the final dosage form is selected from the group consisting of a tablet, a powder, a capsule, a blister pack, an inhaler, and a vial. According to another embodiment, the final dosage form is a substantially uniform pharmaceutical tablet containing the at least one active pharmaceutical ingredient (API) impregnated porous carrier. According to another embodiment, the final dosage form is a substantially uniform pharmaceutical powder containing the at least one active pharmaceutical ingredient (API) impregnated porous carrier. According to another embodiment, the final dosage form is a capsule containing the at least one active pharmaceutical ingredient (API) impregnated porous carrier. According to another embodiment, the final dosage form is a blister pack containing the at least one active pharmaceutical ingredient (API) impregnated porous carrier. According to another embodiment, the final dosage form is an inhaler containing the at least one active pharmaceutical ingredient (API) impregnated porous carrier. According to another embodiment, the final dosage form is a vial containing a substantially uniform powder blend containing the at least one active pharmaceutical ingredient (API) impregnated porous carrier. According to another embodiment, the method further comprises milling and further processing the at least one active pharmaceutical ingredient (API) impregnated porous carrier. According to another embodiment, the method further comprises lubricating and further processing the at least one active pharmaceutical ingredient (API) impregnated porous carrier. According to another embodiment, the method further comprises preparing a final dosage form, wherein the final dosage form is selected from the group consisting of a tablet, a powder, a capsule, a blister pack, an inhaler, and a vial, and wherein the final dosage form produced has enhanced bioavailability. According to another embodiment, the final dosage form is a substantially uniform pharmaceutical tablet containing the at least one active pharmaceutical ingredient (API) impregnated porous carrier. According to another embodiment, the final dosage form is a substantially uniform pharmaceutical powder containing the at least one active pharmaceutical ingredient (API) impregnated porous carrier. According to another embodiment, the final dosage form is a capsule containing the at least one active pharmaceutical ingredient (API) impregnated porous carrier. According to another embodiment, the final dosage form is a blister pack containing the at least one active pharmaceutical ingredient (API) impregnated porous carrier. According to another embodiment, the final dosage form is an inhaler containing the at least one active pharmaceutical ingredient (API) impregnated porous carrier. According to another embodiment, the final dosage form is a vial containing a substantially uniform powder blend containing the at least one active pharmaceutical ingredient (API) impregnated porous carrier.

According to another aspect, the described invention provides an active pharmaceutical ingredient (API)-impregnated porous carrier, wherein at least one active pharmaceutical ingredient (API) is impregnated throughout an internal surface of a porous carrier.

According to one embodiment, the at least one active pharmaceutical ingredient (API) comprises acetaminophen, ibuprofen, indometacin/indomethacin, flufenamic acid, Imatinib, flufenamic acid, erlotinib hydrochloride, vitamin D, a steroid, estrodial, or a combination thereof. According to another embodiment, the porous carrier is of a high porosity of 20% to 80% pores by volume. According to another embodiment, the porous carrier has a high specific surface area. According to another embodiment, the porous carrier is a pharmaceutical carrier. According to another embodiment, the porous carrier is $CaHPO_4$. According to another embodiment, the porous carrier is anhydrous $CaHPO_4$.

BRIEF DESCRIPTION OF THE DRAWINGS

FIG. 1 shows an illustrative fluidized bed impregnation system.

FIG. 2A shows photomicrographs of $CaHPO_4$-Emcompress®, a preformed porous carrier.

FIG. 4A shows a graph of DSC analysis of sieved impregnated fractions.

FIG. 8A shows a dissolution profile of impregnated $CaHPO_4$ with acetaminophen (APAP) to a loading level of 1%. FIG. 8B shows a dissolution profile of impregnated $CaHPO_4$ with acetaminophen (APAP) to a loading level of 8.8%. The experiments were done using baskets instead of paddles, which are more appropriate and accurate when testing dissolution profiles of capsules. The percentage of acetaminophen (APAP) dissolved showing over 100% in FIG. 8B can be attributed to the following: (1) small errors in the calibration curve used; (2) small error in weighing of the capsules; or (3) some moisture content in the blend due to uncontrolled storage conditions.

FIG. 9A shows a plot of particle size distributions for pure $CaHPO_4$, impregnated $CaHPO_4$ (high and low loadings) and milled impregnated $CaHPO_4$ (high and low loadings). FIG. 9B shows numerical data of particle size distributions for pure $CaHPO_4$, impregnated $CaHPO_4$ (high and low loadings) and milled impregnated $CaHPO_4$ (high and low loadings).

FIG. 10 shows (left panel) a graph of tablet hardness (N) versus compression force (kN).

FIG. 14 shows blend uniformity results for impregnation experiments using a second model drug (Ibuprofen). The results indicate that the manufacturing method of the invention is not limited to only acetaminophen (APAP) but can be used for any other drug.

FIG. 15 shows DSC scans of various size fractions of impregnated CaHPO$_4$ with Ibuprofen. The plots show an absence of amorphous content (upward peaks). They also show broadening of the melting peaks of Ibuprofen and shifting to lower melting points (pure Ibuprofen melts at 77.3° C.).

FIG. 16 shows a dissolution profile of gelatin capsules filled with CaHPO$_4$ impregnated with Ibuprofen at 10% loading.

DETAILED DESCRIPTION OF THE INVENTION

Figure 2B:
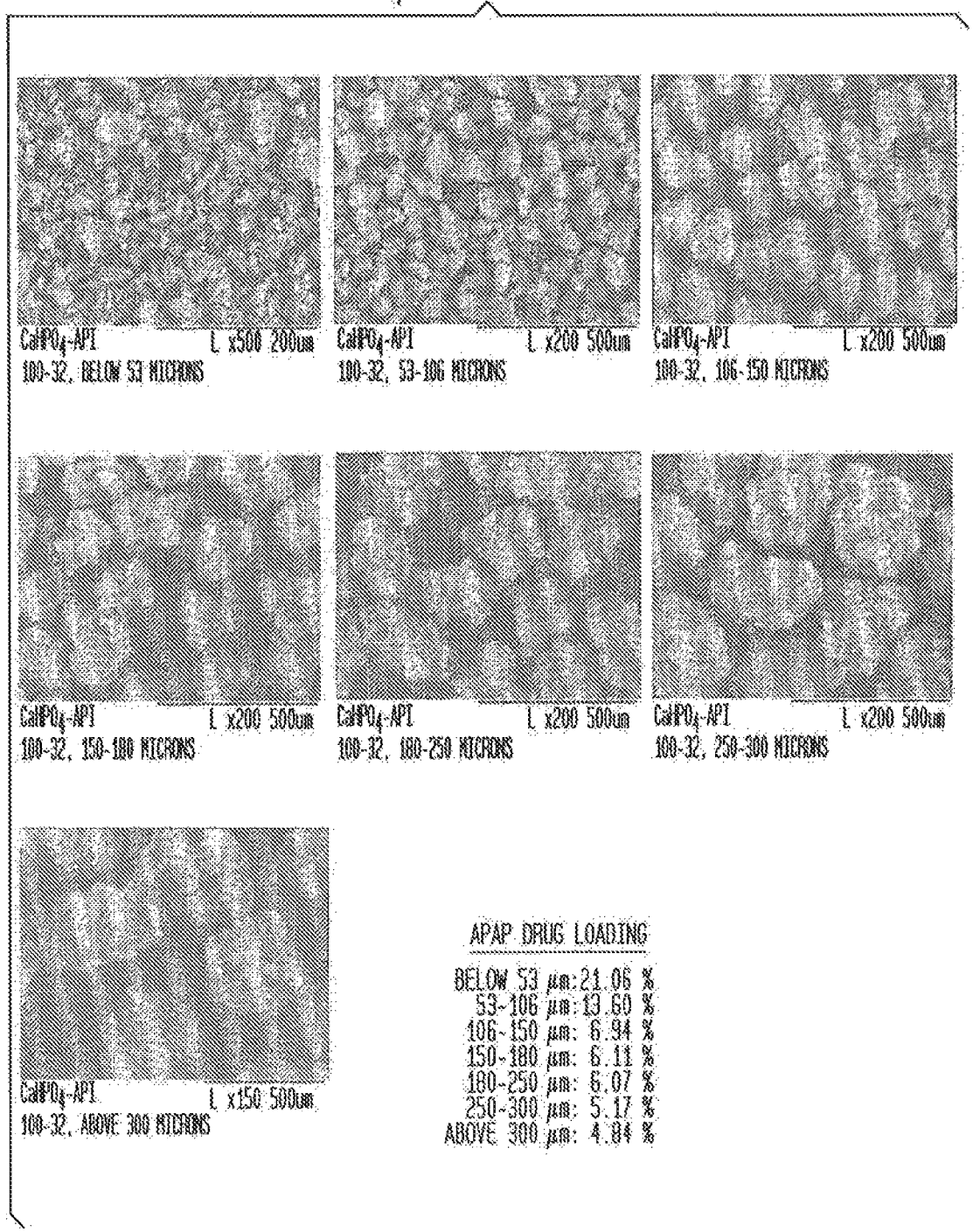
FIG. 2B shows photomicrographs of $CaHPO_4$ impregnated with acetaminophen (APAP).

The described invention provides a method for impregnating a drug solution throughout the volume of a porous carrier by spraying the solution onto the carrier in a fluid bed processor, an agitated vessel, or a tumbling vessel, or other suitable means for ensuring uniform contact between the porous carrier and the solution. The liquid medium used to create said solution, hereafter referred to as the "solvent," is chosen to have high vapor pressure and low surface tension on porous carrier surfaces. Upon contact, capillary forces drive the solution into the porous carrier. The solvent is concurrently or subsequently evaporated in a fluid bed, in an agitated vessel, in a tumbler, in a tray oven, or any other device that provides uniform contact between the impregnated material and a drying source, such as, but not limited to, dry air, providing a substantially uniform composite particle of the carrier and the drug(s). Since the drug is deposited on the internal surface of the carrier, the external surface properties of the carrier remain largely unchanged regardless of the concentration of drug, or even the type of drug deposited. The dried carrier can be subsequently milled to further improve uniformity, and then filled into capsules, vials, aerosol blisters, or compressed into tablets.

A method known as "incipient wetness impregnation" uses capillary forces to impregnate porous carriers in an extremely uniform manner; here, solutions are impregnated onto porous carriers as a convenient method for distributing small amounts of precious metals onto porous carriers. The method is usually implemented in, for example, but not limited to, large tumbler mixers equipped with spray nozzles and jacketed to allow heat exchange.

A fluidized bed (FIG. 1) provides a very high degree of mixing for the carrier to be impregnated. As the API solution is sprayed into the fluidized bed, the spray nozzle produces very tiny droplets, a few microns in diameter. These droplets containing API collide with individual carrier particles in the so called "spray zone" and these wetted particles are then carried away. As they move throughout the fluidized bed they begin to dry. If the temperature of the fluidization gas is high enough, these droplets will dry immediately after collision, resulting in carrier particles coated with API. If, however, the drying temperature is chosen carefully (not very high), the droplets will have enough time to penetrate the carrier particles due to capillary forces. The solvent is subsequently evaporated leaving the API inside the porous carrier. The process is repeated as these particles re-enter the spray zone. Therefore, this process can be viewed also as a multistage impregnation. Due to the very good mixing inside the fluidized bed and the small droplets continuously impregnating all individual porous particles, this process yields very high uniformity in the API distribution within the carrier. An important scale-up parameter that has a significant impact on the API distribution is the spray rate, defined as:

$$\text{Spray Rate} = ((m(\text{API sprayed}))/(\text{Spray Time} * m(\text{carrier})))$$

The smaller the spray rate, the higher the API uniformity, where m(API sprayed) is the mass of API sprayed and m(carrier) is the mass of the carrier. In general, for a given mass of API and carrier to be impregnated, the longer the time for spraying is (or lower initial API concentration in the solvent) the higher the API uniformity within the blend will be. This parameter provides for a high blend uniformity for very low drug loadings, and makes blend uniformity virtually independent of the drug loading.

The impregnation process also can be performed in additional forms, including, but not limited to, the use of agitated vessels and tumblers. The drying process also can be performed in additional forms, including, but not limited to, the use of agitated vessels, tumblers, and tray ovens, or combinations thereof.

The independence of the blend uniformity from the drug loading holds true if the porosity of the porous carrier is independent of particle size, and is further promoted if the particles have uniform size. In that case, all particles moving in the fluidized bed spend largely the same time in the spray zone receiving the same amount of drug per particle. In practice, however, there is always some particle size and porosity distribution associated with the carrier. The flow pattern will be different for different size groups resulting in uneven drug uptake during impregnation. Even if all particles receive the same amount of API, the drug loading per unit mass will be different for each size group due to time delays incurred in impregnating the larger particles, the possibility of saturating smaller particles, and then coating their external surface. As a result, in some cases, small particles will end up with higher percent loading compared to large particles. This variation combined with the fact that there will be some segregation between particles due to their size differences, will result in a small degree of API content variability in the blend. Milling the final impregnated material significantly reduces this variability. Breaking large particles results in smaller ones, some of which will have drug in them and some of which will have less. This in turn will cause the API variability to be decreased in two ways. First, it will minimize segregation since the size difference is now less pronounced. Second, small particles that have less drug in them (as a result of milling) generally will not be a problem, since they will be uniformly distributed within the blend and their segregation will be minimized based on the above rationale. On the other hand, excessively intense milling will reduce the flowability of the final powder. Therefore, a balance between milling intensity and improved API variability is needed. Gentle milling can reduce variability by half (or more in some cases) without affecting the flow properties of the impregnated material.

1. Method for Impregnating a Porous Carrier with an Active Pharmaceutical Ingredient According to one aspect, the described invention provides a method for impregnating a porous carrier with an active pharmaceutical ingredient ("API"), the method comprising steps:

a) dissolving at least one API in a solvent to form a API solution;

b) contacting a porous carrier with the at least one API of step (a) in a contactor to form an API impregnated porous carrier;

c) drying the API impregnated porous carrier; and d) optionally milling the API impregnated porous carrier of (c).

Solvent

According to one embodiment, the solvent is a solvent appropriate for the API. According to one embodiment, the solvent is of a low boiling point. According to another embodiment, the solvent is a green solvent.

According to another embodiment, the API solution is of a desired concentration. According to some such embodiments, the desired concentration is of a therapeutically effective amount.

According to another embodiment, the solvent provides good wettability.

According to another embodiment, the solvent is not detrimental to the API.

According to another embodiment, the solvent has at least one of the following properties: ability to dissolve the API in appropriate concentrations, low surface tension on carrier surfaces, high vapor pressure, low toxicity, and low or null explosivity, or combinations thereof.

Porous Carrier

According to another embodiment, the porous carrier is of a high porosity. According to some such embodiments, the porous carrier has a high specific surface area.

According to another embodiment, step (d) provides good flowability. According to another embodiment, step (d) provides tight particle size distribution (PSD) of the carrier.

According to some embodiments, the carrier is a pharmaceutical carrier. According to some embodiments, the carrier is $CaHPO_4$. According to some embodiments, the pharmaceutical carrier is anhydrous $CaHPO_4$-Emcompress®.

Contacting the API Solution

According to another embodiment, contacting step (b) comprises spraying. According to another embodiment, the spray rate is adjustable. According to another embodiment, the spray rate is a controlled spray rate. According to another embodiment, the spray rate allows for scale-up.

According to another embodiment, spraying is stopped when the desired API content has been achieved.

According to some embodiments, the API impregnated porous carrier can be blended with a different API or an excipient. According to one embodiment, the blend comprises at least one API and at least one API impregnated porous carrier. According to one embodiment, the blend comprises at least one API impregnated porous carrier and one excipient to facilitate downstream processing.

According to another embodiment, the blend comprising the API and porous carrier is dried. According to some such embodiments, the blend is dried until a desired residual solvent content has been reached.

According to another embodiment, the atomization pressure is a controlled atomization pressure. According to some such embodiments, the atomization pressure is an adjustable atomization pressure.

According to another embodiment, the contacting temperature is of a temperature appropriate for the solvent.

According to some embodiments, the contactor is a fluidized bed. According to some embodiments, the contactor is an agitated vessel. According to some embodiments, the contactor is a tumbler. According to some embodiments, the contactor is a stirred vessel. According to some embodiments, the contactor is a tray oven.

According to another embodiment, the API solution is sprayed onto the carrier in a contactor. According to another embodiment, the API solution is sprayed onto the porous carrier in a contactor, wherein the contactor is an agitated vessel. According to another embodiment, the API solution is sprayed onto the carrier in a contactor, wherein the contactor is a tumbler.

Drying the API Impregnated Porous Carrier

According to another embodiment, the API impregnated porous carrier is dried in a contactor. According to some embodiments, the API impregnated porous carrier is dried in the contactor of step (b). According to another embodiment, the API impregnated porous carrier is dried in a contactor, wherein the contactor is an agitated vessel. According to another embodiment, the API impregnated porous carrier is dried in a contactor, wherein the contactor is a tumbler. According to another embodiment, the API impregnated porous carrier is dried in a contactor, wherein the contactor is a tray oven.

According to another embodiment, the API impregnated porous carrier is dried in parallel with contacting step (b). According to another embodiment, the API impregnated porous carrier is dried after contacting step (b).

Milling

According to another embodiment, the API impregnated porous carrier ("impregnated carrier") is milled to improve blend uniformity.

According to another embodiment, the milling is gentle milling.

According to another embodiment, the impregnated carrier comprises from about 10% API w/w/to about 0.1% API w/w.

2. API Impregnated Fluidized Porous Carrier

According to another aspect, the described invention provides an API-impregnated porous carrier comprising an API impregnated porous carrier fabricated by a method comprising steps:

a) dissolving at least one API in a solvent to form a API solution;

b) contacting a porous carrier with the at least one API of step (a) in a contactor to form an API impregnated porous carrier;

c) drying the API impregnated porous carrier; and d) optionally milling the API impregnated porous carrier of (c).

Solvent

According to one embodiment, the solvent is a solvent appropriate for the API. According to one embodiment, the solvent is of a low boiling point. According to another embodiment, the solvent is a green solvent. According to another embodiment, the solvent is an inorganic or organic solvent including, but not limited to, ethanol, methanol, isopropyl alcohol (IP A), acetone, 1-propanol, 1-pentanol, acetonitrile, butanol, methyl ethyl ketone (MEK), methyl acetate, 2-methyl tetrahydrofuran, isopropyl acetate (IPAc), n-hexane, ethyl acetate (EtOAc), n-heptane, water, an aqueous solvent or supercritical $CO_2$.

According to another embodiment, the API solution is of a desired concentration. According to some such embodiments, the desired concentration is of a therapeutically effective amount.

According to another embodiment, the therapeutically effective amount is $10^{-6}$ weight % to 40 weight % of API in the solvent. According to another embodiment, the therapeutically effective amount is $10^{-6}$ weight % to 35 weight % of API in the solvent. According to another embodiment, the therapeutically effective amount is $10^{-6}$ weight % to 30 weight % of API in the solvent. According to another embodiment, the therapeutically effective amount is $10^{-6}$ weight % to 25 weight % of API in the solvent. According to another embodiment, the therapeutically effective amount is $10^{-6}$ weight % to 20 weight % of API in the solvent. According to another embodiment, the therapeutically effective amount is $10^{-6}$ weight % to 15 weight % of API in the solvent. According to another embodiment, the therapeutically effective amount is $10^{-6}$ weight % to 10 weight % of API in the solvent. According to another embodiment, the therapeutically effective amount is $10^{-6}$ weight % to 5 weight % of API in the solvent. According to another embodiment, the therapeutically effective amount is $10^{-6}$ weight % to 1 weight % of API in the solvent.

According to another embodiment, the therapeutically effective amount is $10^{-5}$ weight % to 40 weight % of API in the solvent. According to another embodiment, the therapeutically effective amount is $10^{-5}$ weight % to 35 weight % of API in the solvent. According to another embodiment, the therapeutically effective amount is $10^{-5}$ weight % to 30 weight % of API in the solvent. According to another embodiment, the therapeutically effective amount is $10^{-5}$ weight % to 25 weight % of API in the solvent. According to another embodiment, the therapeutically effective amount is $10^{-5}$ weight % to 20 weight % of API in the solvent. According to another embodiment, the therapeutically effective amount is $10^{-5}$ weight % to 15 weight % of API in the solvent. According to another embodiment, the therapeutically effective amount is $10^{-5}$ weight % to 10 weight % of API in the solvent. According to another embodiment, the therapeutically effective amount is $10^{-5}$ weight % to 5 weight % of API in the solvent. According to another embodiment, the therapeutically effective amount is $10^{-5}$ weight % to 1 weight % of API in the solvent.

According to another embodiment, the therapeutically effective amount is $10^{-4}$ weight % to 40 weight % of API in the solvent. According to another embodiment, the therapeutically effective amount is $10^{-4}$ weight % to 35 weight % of API in the solvent. According to another embodiment, the therapeutically effective amount is $10^{-4}$ weight % to 30 weight % of API in the solvent. According to another embodiment, the therapeutically effective amount is $10^{-4}$ weight % to 25 weight % of API in the solvent. According to another embodiment, the therapeutically effective amount is $10^{-4}$ weight % to 20 weight % of API in the solvent. According to another embodiment, the therapeutically effective amount is $10^{-4}$ weight % to 15 weight % of API in the solvent. According to another embodiment, the therapeutically effective amount is $10^{-4}$ weight % to 10 weight % of API in the solvent. According to another embodiment, the therapeutically effective amount is $10^{-4}$ weight % to 5 weight % of API in the solvent. According to another embodiment, the therapeutically effective amount is $10^{-4}$ weight % to 1 weight % of API in the solvent.

According to another embodiment, the therapeutically effective amount is $10^{-3}$ weight % to 40 weight % of API in the solvent. According to another embodiment the therapeutically effective amount is $10^{-3}$ weight % to 35 weight % of API in the solvent. According to another embodiment, the therapeutically effective amount is $10^{-3}$ weight % to 30 weight % of API in the solvent. According to another embodiment, the therapeutically effective amount is $10^{-3}$ weight % to 25 weight % of API in the solvent. According to another embodiment, the therapeutically effective amount is $10^{-3}$ weight % to 20 weight % of API in the solvent. According to another embodiment, the therapeutically effective amount is $10^{-3}$ weight % to 15 weight % of API in the solvent. According to another embodiment, the therapeutically effective amount is $10^{-3}$ weight % to 10 weight % of API in the solvent. According to another embodiment, the therapeutically effective amount is $10^{-3}$ weight % to 5 weight % of API in the solvent. According to another embodiment, the therapeutically effective amount is $10^{-3}$ weight % to 1 weight % of API in the solvent.

According to another embodiment, the therapeutically effective amount is $10^{-2}$ weight % to 40 weight % of API in the solvent. According to another embodiment, the therapeutically effective amount is $10^{-2}$ weight % to 35 weight % of API in the solvent. According to another embodiment, the therapeutically effective amount is $10^{-2}$ weight % to 30 weight % of API in the solvent. According to another embodiment, the therapeutically effective 2 amount is $10^{-2}$ weight % to 25 weight % of API in the solvent. According to another embodiment, the therapeutically effective amount is $10^{-2}$ weight % to 20 weight % of API in the solvent. According to another embodiment, the therapeutically effective amount is $10^{-2}$ weight % to 15 weight % of API in the solvent. According to another embodiment, the therapeutically effective amount is $10^{-2}$ weight % to 10 weight % of API in the solvent. According to another embodiment, the therapeutically effective amount is $10^{-2}$ weight % to 5 weight % of API in the solvent. According to another embodiment, the therapeutically effective amount is $10^{-2}$ weight % to 1 weight % of API in the solvent.

According to another embodiment, the therapeutically effective amount is 0.1 weight % to 40 weight % of API in the solvent. According to another embodiment, the therapeutically effective amount is 0.1 weight % to 35 weight % of API in the solvent. According to another embodiment, the therapeutically effective amount is 0.1 weight % to 30 weight % of API in the solvent. According to another embodiment, the therapeutically effective amount is 0.1 weight % to 25 weight % of API in the solvent. According to another embodiment, the therapeutically effective amount is 0.1 weight % to 20 weight % of API in the solvent. According to another embodiment, the therapeutically effective amount is 0.1 weight % to 15 weight % of API in the solvent. According to another embodiment, the therapeutically effective amount is 0.1 weight % to 10 weight % of API in the solvent. According to another embodiment, the therapeutically effective amount is 0.1 weight % to 1 weight % of API in the solvent.

According to another embodiment, the therapeutically effective amount is 1 weight % to 40 weight % of API in the solvent. According to another embodiment, the therapeutically effective amount is 1 weight % to 35 weight % of API in the solvent. According to another embodiment, the therapeutically effective amount is 1 weight % to 30 weight % of API in the solvent. According to another embodiment, the therapeutically effective amount is 1 weight % to 25 weight % of API in the solvent. According to another embodiment, the therapeutically effective amount is 1 weight % to 20 weight % of API in the solvent. According to another embodiment, the therapeutically effective amount is 1 weight % to 15 weight % of API in the solvent. According to another embodiment, the therapeutically effective amount is 1 weight % to 10 weight % of API in the solvent. According to another embodiment, the therapeutically effective amount is 1 weight % to 5 weight % of API in the solvent.

According to another embodiment, the therapeutically effective amount is 5 weight % to 10 weight % of API in the solvent. According to another embodiment, the therapeutically effective amount is 10 weight % to 15 weight % of API in the solvent. According to another embodiment, the therapeutically effective amount is 15 weight % to 20 weight % of API in the solvent. According to another embodiment, the therapeutically effective amount is 20 weight % to 25 weight % of API in the solvent. According to another embodiment, the therapeutically effective amount is 25 weight % to 30 weight % of API in the solvent. According to another embodiment, the therapeutically effective amount is 30 weight % to 35 weight % of API in the solvent. According to another embodiment, the therapeutically effective amount is 35 weight % to 40 weight % of API in the solvent.

According to another embodiment, the solvent provides good wettability.

According to another embodiment, the solvent is not detrimental to the API.

According to another embodiment, the solvent has at least one of the following properties: ability to dissolve the API in appropriate concentrations, low surface tension on carrier surfaces, high vapor pressure, low toxicity, and low or null explosivity, or combinations thereof.

Porous Carrier

According to another embodiment, the porous carrier is of a high porosity. According to some such embodiments, the porous carrier has a high specific surface area. According to another embodiment, the porosity of the carrier ranges from 20% to 80% pores by volume. According to another embodiment, the porosity of the carrier ranges from 20% to 75% pores by volume. According to another embodiment, the porosity of the carrier ranges from 20% to 70% pores by volume. According to another embodiment, the porosity of the carrier ranges from 20% to 65% pores by volume. According to another embodiment, the porosity of the carrier ranges from 20% to 60% pores by volume. According to another embodiment, the porosity of the carrier ranges from 20% to 55% pores by volume. According to another embodiment, the porosity of the carrier ranges from 20% to 50% pores by volume. According to another embodiment, the porosity of the carrier ranges from 20% to 45% pores by volume. According to another embodiment, the porosity of the carrier ranges from 20% to 40% pores by volume. According to another embodiment, the porosity of the carrier ranges from 20% to 35% pores by volume. According to another embodiment, the porosity of the carrier ranges from 20% to 30% pores by volume. According to another embodiment, the porosity of the carrier ranges from 20% to 25% pores by volume. According to another embodiment, the porosity of the carrier ranges from 25% to 30% pores by volume. According to another embodiment, the porosity of the carrier ranges from 30% to 35% pores by volume. According to another embodiment, the porosity of the carrier ranges from 35% to 40% pores by volume. According to another embodiment, the porosity of the carrier ranges from 40% to 45% pores by volume. According to another embodiment, the porosity of the carrier ranges from 45% to 50% pores by volume. According to another embodiment, the porosity of the carrier ranges from 50% to 55% pores by volume. According to another embodiment, the porosity of the carrier ranges from 55% to 60% pores by volume. According to another embodiment, the porosity of the carrier ranges from 60% to 65% pores by volume. According to another embodiment, the porosity of the carrier ranges from 65% to 70% pores by volume. According to another embodiment, the porosity of the carrier ranges from 70% to 75% pores by volume. According to another embodiment, the porosity of the carrier ranges from 75% to 80% pores by volume.

According to another embodiment, step (b) provides good flowability. According to another embodiment, step (b) provides tight particle size distribution (PSD) of the carrier.

According to some embodiments, the carrier is a pharmaceutical carrier. According to some embodiments, the carrier is $CaHPO_4$. According to some embodiments, the pharmaceutical carrier is anhydrous $CaHPO_4$-Emcompress®.

Contacting the API Solution

According to another embodiment, contacting step (b) comprises spraying. According to another embodiment, the spray rate is adjustable. According to another embodiment, the spray rate is a controlled spray rate. According to another embodiment, the spray rate allows for scale-up.

According to another embodiment, spraying is stopped when the desired API content has been achieved.

According to some embodiments, the API impregnated porous carrier is a blend. According to some embodiments, the blend comprises at least one API and at least one porous carrier.

According to another embodiment, the blend comprising the API and porous carrier is dried. According to some such embodiments, the blend is dried until a suitable residual solvent content has been reached. The residual solvent content is the amount of solvent that remains in the carrier after drying. Depending on the choice of solvent and its toxicity the residual solvent content must be below specified limits regulated by the FDA.

According to another embodiment, the contacting temperature is of a temperature appropriate for the solvent. According to another embodiment, the solvent is methanol and the contacting temperature is 25° C. to 55° C. According to another embodiment, the solvent is methanol and the contacting temperature is 25° C. to 50° C. According to another embodiment, the solvent is methanol and the contacting temperature is 25° C. to 45° C. According to another embodiment, the solvent is methanol and the contacting temperature is 25° C. to 40° C. According to another embodiment, the solvent is methanol and the contacting temperature is 25° C. to 35° C. According to another embodiment, the solvent is methanol and the contacting temperature is 25° C. to 30° C. According to another embodiment, the solvent is methanol and the contacting temperature is 30° C. to 35° C. According to another embodiment, the solvent is methanol and the contacting temperature is 35° C. to 40° C. According to another embodiment, the solvent is methanol and the contacting temperature is 40° C. to 45° C. According to another embodiment, the solvent is methanol and the contacting temperature is 45° C. to 50° C. According to another embodiment, the solvent is methanol and the contacting temperature is 50° C. to 55° C.

According to another embodiment, the atomization pressure is a controlled atomization pressure. According to some such embodiments, the atomization pressure is an adjustable atomization pressure.

According to some embodiments, the contactor is a fluidized bed. According to some embodiments, the contactor is an agitated vessel. According to some embodiments, the contactor is a tumbler. According to some embodiments, the contactor is a stirred vessel. According to some embodiments, the contactor is a tray oven.

According to another embodiment, the porous carrier is impregnated in a contactor, wherein the contactor is a fluidized bed. According to another embodiment, the porous carrier is impregnated in a contactor, wherein the contactor is a stirred vessel. According to another embodiment, the porous carrier is impregnated in a contactor, wherein the contactor is a tumbler.

Drying the API Impregnated Porous Carrier

According to another embodiment, the API impregnated porous carrier is dried in a contactor. According to some embodiments, the API impregnated porous carrier is dried in the contactor of step (b). According to another embodiment, the API impregnated porous carrier is dried in a contactor, wherein the contactor is an agitated vessel. According to another embodiment, the API impregnated porous carrier is dried in a contactor, wherein the contactor is a tumbler. According to another embodiment, the API impregnated porous carrier is dried in a contactor, wherein the contactor is a tray oven.

According to another embodiment, the API impregnated porous carrier is dried in parallel with contacting step (b). According to another embodiment, the API impregnated porous carrier is dried after contacting step (b).

Milling

According to another embodiment, the API impregnated porous carrier ("impregnated carrier") is milled to improve blend uniformity. According to one embodiment, the particles are milled to obtain particles with a $D_{90}$ of less than 200 microns. According to another embodiment, the particles are milled to obtain particles with a $D_{90}$ of less than 150 microns. According to another embodiment, the particles are milled to obtain particles with a $D_{90}$ of less than 100 microns. According to another embodiment, the particles are milled to obtain particles with a $D_{90}$ of less than 50 microns. According to another embodiment, the particles are milled to obtain particles with a $D_{90}$ of less than 10 microns. According to another embodiment, the particles are milled to obtain particles with a $D_{90}$ of less than 1 microns.

According to another embodiment, the milling is gentle milling.

According to another embodiment, the blend comprises from about 10% API w/w/to about 0.1% API w/w.

Additional Embodiments

According to the described invention, additional embodiments include, but are not limited to, a method, based on fluid bed impregnation, for distributing one or more active substances across the volume of a preformed porous carrier.

According to another embodiment, the described invention provides a method, based on fluid bed impregnation, for achieving a substantially uniform distribution of one or more active substances across the volume of a preformed porous carrier.

The term "substantially uniform distribution of one or more active substances" as used herein refers to an amount of one or more active substances, such that any single active substance content variability in a finished drug product has a relative standard deviation (RSD) of less than 3%. According to another embodiment, the single active substance content variability in a finished drug product has a relative standard deviation (RSD) of less than 2.5%. According to another embodiment, the single active substance content variability in a finished drug product has a relative standard deviation (RSD) of less than 2%. According to another embodiment, the single active substance content variability in a finished drug product has a relative standard deviation (RSD) of less than 1.5%. According to another embodiment, the single active substance content variability in a finished drug product has a relative standard deviation (RSD) of less than 1%. According to another embodiment, the single active substance content variability in a finished drug product has a relative standard deviation (RSD) of less than 0.5%. According to another embodiment, the single active substance content variability in a finished drug product has a relative standard deviation (RSD) of less than 0.1%.

According to another embodiment, the described invention provides a method, based on fluid bed impregnation, for achieving substantially uniform distribution of one or more active substances across the volume of a preformed porous carrier, followed by a additional powder processing steps, to be used for making substantially uniform pharmaceutical products containing one of more active substances.

According to another embodiment, the described invention provides a method, based on fluid bed impregnation, for achieving substantially uniform distribution of one or more active substances across the volume of a preformed porous carrier, followed by a direct compression step, to be used for making substantially uniform pharmaceutical tablets containing one of more active substances.

The tablet, the most frequently prescribed commercial dosage form, is stable, elegant, and effective. It provides the patient with a convenient product for handling, identification, and administration. Tablets can be prepared using pellet presses or tableting machines. Non-limiting examples of tablets include, but are not limited to, sublingual molded tablets, buccal molded tablets, sintered tablets, compressed tablets, chewable tablets, soluble effervescent tablets, and implants or pellets.

According to another embodiment, the described invention provides a method, based on fluid bed impregnation, for achieving substantially uniform distribution of one or more active substances across the volume of a preformed porous carrier, followed by a capsule filling step, to be used for making substantially uniform pharmaceutical capsules containing one of more active substances.

Capsules are solid dosage forms in which the drug is enclosed within either a hard or soft soluble container or shell. Capsules are generally of the hard gelatin or soft gelatin type. Hard gelatin capsules can be prepared to release the drug rapidly or over a predetermined time, whereas soft gelatin capsules provide standard release. Hard gelatin capsules consist of two parts: the base and body, which is longer and has a lesser diameter. This dosage form is intended to be swallowed whole.

According to another embodiment, the described invention provides a method, based on fluid bed impregnation, for achieving substantially uniform distribution of one or more active substances across the volume of a preformed porous carrier, followed by an inhaler filling step, to be used for making substantially uniform pharmaceutical inhalers containing one of more active substances.

Inhalation is a method of drug delivery where a dose of a drug incorporated in a properly designed dosage form is introduced through the mouth or nose of a patient. The drug is then caught up in the flow of air and carried into the deep recesses of the pulmonary environment, i.e., into the respiratory bronchioles and the alveolar region. Drugs can take the form of a vapor, a very fine powder, or solution in the form of an aerosol. A wide range of dosage forms and methods of administering drugs by inhalation is available including, but not limited to, aerosols, inhalations, insufflations, metered-dose inhalers (MDIs), nebulizers, and vaporizers. Inhalants are drugs that can be carried by an air current into the nasal passage where the drugs generally exert their effect. The device or the container from which the inhalant is generally administered is called an inhaler.

According to another embodiment, the described invention provides a method, based on fluid bed impregnation, for achieving substantially uniform distribution of one or more active substances across the volume of a preformed porous carrier, followed by a blister filling step, to be used for making substantially uniform pharmaceutical inhalation products containing one of more active substances.

Blister packs, which are commonly used as unit-dose packaging for pharmaceutical powders, tablets, capsules or lozenges, can provide barrier protection for shelf life requirements, and a degree of tamper resistance. Blister packs are created by means of form-fill-seal process wherein the blister packs are created from rolls of flat sheet or film, filled with the pharmaceutical product and closed (sealed) on the same equipment called blisterline.

According to another embodiment, the described invention provides a method, based on fluid bed impregnation, for achieving substantially uniform distribution of one or more active substances across the volume of a preformed porous carrier, followed by a vial filling step, to be used for making vials containing substantially uniform powder blends for pharmaceutical applications containing one or more active substances.

According to another embodiment, the described invention provides a method, based on fluid bed impregnation, for achieving substantially uniform distribution of one or more active substances across the volume of a preformed porous carrier, followed by a milling step and additional powder processing steps, to be used for making substantially uniform pharmaceutical products containing one of more active substances.

According to another embodiment, the described invention provides a method, based on fluid bed impregnation, for achieving substantially uniform distribution of one or more active substances across the volume of a preformed porous carrier, followed by a milling step and additional powder processing steps, to be used for making substantially uniform pharmaceutical products containing one of more active substances, followed by a direct compression step, to be used for substantially uniform making pharmaceutical tablets containing one of more active substances.

According to another embodiment, the described invention provides a method, based on fluid bed impregnation, for achieving substantially uniform distribution of one or more active substances across the volume of a preformed porous carrier, followed by a milling step and additional powder processing steps, to be used for making substantially uniform pharmaceutical products containing one of more active substances, followed by a capsule filling step, to be used for making substantially uniform pharmaceutical capsules containing one of more active substances.

According to another embodiment, the described invention provides a method, based on fluid bed impregnation, for achieving substantially uniform distribution of one or more active substances across the volume of a preformed porous carrier, followed by a milling step and additional powder processing steps, to be used for making substantially uniform pharmaceutical products containing one of more active substances, followed by an inhaler filling step, to be used for making substantially uniform pharmaceutical inhalers containing one of more active substances.

According to another embodiment, the described invention provides a method, based on fluid bed impregnation, for achieving substantially uniform distribution of one or more active substances across the volume of a preformed porous carrier, followed by a milling step and additional powder processing steps, to be used for making substantially uniform pharmaceutical products containing one of more active substances, followed by a blister filling step, to be used for making substantially uniform pharmaceutical inhalation products containing one of more active substances.

According to another embodiment, the described invention provides a method, based on fluid bed impregnation, for achieving substantially uniform distribution of one or more active substances across the volume of a preformed porous carrier, followed by a milling step and additional powder processing steps, to be used for making substantially uniform pharmaceutical products containing one of more active substances, followed by a vial filling step, to be used for making vials containing substantially uniform powder blends for pharmaceutical applications containing one of more active substances.

According to another embodiment, the described invention provides a method, based on fluid bed impregnation, for achieving substantially uniform distribution of one or more active substances across the volume of a preformed porous carrier, followed by a lubrication step and additional powder processing steps, to be used for making substantially uniform pharmaceutical products containing one of more active substances.

According to another embodiment, the described invention provides a method, based on fluid bed impregnation, for achieving substantially uniform distribution of one or more active substances across the volume of a preformed porous carrier, followed by a lubrication step and additional powder processing steps, to be used for making substantially uniform pharmaceutical products containing one of more active substances, followed by a direct compression step, to be used for making substantially uniform pharmaceutical tablets containing one of more active substances.

According to another embodiment, the described invention provides a method, based on fluid bed impregnation, for achieving substantially uniform distribution of one or more active substances across the volume of a preformed porous carrier, followed by a lubrication step and additional powder processing steps, to be used for making substantially uniform pharmaceutical products containing one of more active substances, followed by a capsule filling step, to be used for making substantially uniform pharmaceutical capsules containing one of more active substances.

According to another embodiment, the described invention provides a method, based on fluid bed impregnation, for achieving substantially uniform distribution of one or more active substances across the volume of a preformed porous carrier, followed by a lubrication step and additional powder processing steps, to be used for making substantially uniform pharmaceutical products containing one of more active substances, followed by an inhaler filling step, to be used for making substantially uniform pharmaceutical inhalers containing one of more active substances.

According to another embodiment, the described invention provides a method, based on fluid bed impregnation, for achieving substantially uniform distribution of one or more active substances across the volume of a preformed porous carrier, followed by a lubrication step and additional powder processing steps, to be used for making substantially uniform pharmaceutical products containing one of more active substances, followed by a blister filling step, to be used for making substantially uniform pharmaceutical inhalation products containing one of more active substances.

According to another embodiment, the described invention provides a method, based on fluid bed impregnation, for achieving substantially uniform distribution of one or more active substances across the volume of a preformed porous carrier, followed by a lubrication step and additional powder processing steps, to be used for making substantially uniform pharmaceutical products containing one of more active substances, followed by a vial filling step, to be used for making vials containing substantially uniform powder blends for pharmaceutical applications containing one of more active substances.

According to another embodiment, the described invention provides a method, based on fluid bed impregnation, for achieving substantially uniform distribution of one or more active substances across the volume of a preformed porous carrier, followed by a milling and a lubrication step, in either order, and additional powder processing steps, to be used for making substantially uniform pharmaceutical products containing one of more active substances.

According to another embodiment, the described invention provides a method, based on fluid bed impregnation, for achieving substantially uniform distribution of one or more active substances across the volume of a preformed porous carrier, followed by a milling and a lubrication step, in either order, and additional powder processing steps, to be used for making substantially uniform pharmaceutical products containing one of more active substances, followed by a direct compression step, to be used for making substantially uniform pharmaceutical tablets containing one of more active substances.

According to another embodiment, the described invention provides a method, based on fluid bed impregnation, for achieving substantially uniform distribution of one or more active substances across the volume of a preformed porous carrier, followed by a milling and a lubrication step, in either order, and additional powder processing steps, to be used for making substantially uniform pharmaceutical products containing one of more active substances, followed by a capsule filling step, to be used for making substantially uniform pharmaceutical capsules containing one of more active substances.

According to another embodiment, the described invention provides a method, based on fluid bed impregnation, for achieving substantially uniform distribution of one or more active substances across the volume of a preformed porous carrier, followed by a milling and a lubrication step, in either order, and additional powder processing steps, to be used for making substantially uniform pharmaceutical products containing one of more active substances, followed by an inhaler filling step, to be used for making substantially uniform pharmaceutical inhalers containing one of more active substances.

According to another embodiment, the described invention provides a method, based on fluid bed impregnation, for achieving substantially uniform distribution of one or more active substances across the volume of a preformed porous carrier, followed by a milling and a lubrication step, in either order, and additional powder processing steps, to be used for making substantially uniform pharmaceutical products containing one of more active substances, followed by a blister filling step, to be used for making substantially uniform pharmaceutical inhalation products containing one of more active substances.

According to another embodiment, the described invention provides a method, based on fluid bed impregnation, for achieving substantially uniform distribution of one or more active substances across the volume of a preformed porous carrier, followed by a milling and a lubrication step, in either order, and additional powder processing steps, to be used for making substantially uniform pharmaceutical products containing one of more active substances, followed by a vial filling step, to be used for making vials containing substantially uniform powder blends for pharmaceutical applications containing one of more active substances.

According to another embodiment, the described invention provides a method, based on fluid bed impregnation, for achieving substantially uniform distribution of one or more active substances across the volume of a preformed porous carrier, followed by additional powder processing steps, to be used for making enhanced bioavailability pharmaceutical products containing one of more active substances.

According to another embodiment, the described invention provides a method, based on fluid bed impregnation, for achieving substantially uniform distribution of one or more active substances across the volume of a preformed porous carrier, followed by a direct compression step, to be used for making enhanced bioavailability pharmaceutical tablets containing one of more active substances.

According to another embodiment, the described invention provides a method, based on fluid bed impregnation, for achieving substantially uniform distribution of one or more active substances across the volume of a preformed porous carrier, followed by a capsule filling step, to be used for making enhanced bioavailability pharmaceutical capsules containing one of more active substances.

According to another embodiment, the described invention provides a method, based on fluid bed impregnation, for achieving substantially uniform distribution of one or more active substances across the volume of a preformed porous carrier, followed by an inhaler filling step, to be used for making enhanced bioavailability pharmaceutical inhalers containing one of more active substances.

According to another embodiment, the described invention provides a method, based on fluid bed impregnation, for achieving substantially uniform distribution of one or more active substances across the volume of a preformed porous carrier, followed by a blister filling step, to be used for making enhanced bioavailability pharmaceutical inhalation products containing one of more active substances.

According to another embodiment, the described invention provides a method, based on fluid bed impregnation, for achieving substantially uniform distribution of one or more active substances across the volume of a preformed porous carrier, followed by a vial filling step, to be used for making vials containing enhanced bioavailability powder blends for pharmaceutical applications containing one of more active substances.

According to another embodiment, the described invention provides a method, based on fluid bed impregnation, for achieving substantially uniform distribution of one or more active substances across the volume of a preformed porous carrier, followed by a milling step and additional powder processing steps, to be used for making substantially uniform pharmaceutical products containing one of more active substances, followed by a direct compression step, to be used for enhanced bioavailability making pharmaceutical tablets containing one of more active substances.

According to another embodiment, the described invention provides a method, based on fluid bed impregnation, for achieving substantially uniform distribution of one or more active substances across the volume of a preformed porous carrier, followed by a milling step and additional powder processing steps, to be used for making substantially uniform pharmaceutical products containing one of more active substances, followed by a capsule filling step, to be used for making enhanced bioavailability pharmaceutical capsules containing one of more active substances.

According to another embodiment, the described invention provides a method, based on fluid bed impregnation, for achieving substantially uniform distribution of one or more active substances across the volume of a preformed porous carrier, followed by a milling step and additional powder processing steps, to be used for making substantially uniform pharmaceutical products containing one of more active substances, followed by an inhaler filling step, to be used for making enhanced bioavailability pharmaceutical inhalers containing one of more active substances.

According to another embodiment, the described invention provides a method, based on fluid bed impregnation, for achieving substantially uniform distribution of one or more active substances across the volume of a preformed porous carrier, followed by a milling step and additional powder processing steps, to be used for making substantially uniform pharmaceutical products containing one of more active substances, followed by a blister filling step, to be used for making enhanced bioavailability pharmaceutical inhalation products containing one of more active substances.

According to another embodiment, the described invention provides a method, based on fluid bed impregnation, for achieving substantially uniform distribution of one or more active substances across the volume of a preformed porous carrier, followed by a milling step and additional powder processing steps, to be used for making substantially uniform pharmaceutical products containing one of more active substances, followed by a vial filling step, to be used for making vials containing enhanced bioavailability powder blends for pharmaceutical applications containing one of more active substances.

According to another embodiment, the described invention provides a method, based on fluid bed impregnation, for achieving substantially uniform distribution of one or more active substances across the volume of a preformed porous carrier, followed by a lubrication step and additional powder processing steps, to be used for making substantially uniform pharmaceutical products containing one of more active substances, followed by a direct compression step, to be used for making enhanced bioavailability pharmaceutical tablets containing one of more active substances.

According to another embodiment, the described invention provides a method, based on fluid bed impregnation, for achieving substantially uniform distribution of one or more active substances across the volume of a preformed porous carrier, followed by a lubrication step and additional powder processing steps, to be used for making substantially uniform pharmaceutical products containing one of more active substances, followed by a capsule filling step, to be used for making enhanced bioavailability pharmaceutical capsules containing one of more active substances.

According to another embodiment, the described invention provides a method, based on fluid bed impregnation, for achieving substantially uniform distribution of one or more active substances across the volume of a preformed porous carrier, followed by a lubrication step and additional powder processing steps, to be used for making substantially uniform pharmaceutical products containing one of more active substances, followed by an inhaler filling step, to be used for making enhanced bioavailability pharmaceutical inhalers containing one of more active substances.

According to another embodiment, the described invention provides a method, based on fluid bed impregnation, for achieving substantially uniform distribution of one or more active substances across the volume of a preformed porous carrier, followed by a lubrication step and additional powder processing steps, to be used for making substantially uniform pharmaceutical products containing one of more active substances, followed by a blister filling step, to be used for making enhanced bioavailability pharmaceutical inhalation products containing one of more active substances.

According to another embodiment, the described invention provides a method, based on fluid bed impregnation, for achieving substantially uniform distribution of one or more active substances across the volume of a preformed porous carrier, followed by a lubrication step and additional powder processing steps, to be used for making substantially uniform pharmaceutical products containing one of more active substances, followed by a vial filling step, to be used for making vials containing enhanced bioavailability powder blends for pharmaceutical applications containing one of more active substances.

According to another embodiment, the described invention provides a method, based on fluid bed impregnation, for achieving substantially uniform distribution of one or more active substances across the volume of a preformed porous carrier, followed by a milling and a lubrication step, in either order, and additional powder processing steps, to be used for making substantially uniform pharmaceutical products containing one of more active substances, followed by a direct compression step, to be used for making enhanced bioavailability pharmaceutical tablets containing one of more active substances.

According to another embodiment, the described invention provides a method, based on fluid bed impregnation, for achieving substantially uniform distribution of one or more active substances across the volume of a preformed porous carrier, followed by a milling and a lubrication step, in either order, and additional powder processing steps, to be used for making substantially uniform pharmaceutical products containing one of more active substances, followed by a capsule filling step, to be used for making enhanced bioavailability pharmaceutical capsules containing one of more active substances.

According to another embodiment, the described invention provides a method, based on fluid bed impregnation, for achieving substantially uniform distribution of one or more active substances across the volume of a preformed porous carrier, followed by a milling and a lubrication step, in either order, and additional powder processing steps, to be used for making substantially uniform pharmaceutical products containing one of more active substances, followed by an inhaler filling step, to be used for making enhanced bioavailability pharmaceutical inhalers containing one of more active substances.

According to another embodiment, the described invention provides a method, based on fluid bed impregnation, for achieving substantially uniform distribution of one or more active substances across the volume of a preformed porous carrier, followed by a milling and a lubrication step, in either order, and additional powder processing steps, to be used for making substantially uniform pharmaceutical products containing one of more active substances, followed by a blister filling step, to be used for making enhanced bioavailability pharmaceutical inhalation products containing one of more active substances.

According to another embodiment, the described invention provides a method, based on fluid bed impregnation, for achieving substantially uniform distribution of one or more active substances across the volume of a preformed porous carrier, followed by a milling and a lubrication step, in either order, and additional powder processing steps, to be used for making substantially uniform pharmaceutical products containing one of more active substances, followed by a vial filling step, to be used for making vials containing enhanced bioavailability powder blends for pharmaceutical applications containing one of more active substances.

According to another embodiment, the described invention provides a material, where one or more active pharmaceutical substances are impregnated throughout the internal surface of a preformed porous carrier. According to another embodiment, the active pharmaceutical substance is at least one therapeutic agent.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any method and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be considered as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.), but some experimental errors and deviations should be accounted for. Unless indicated otherwise, parts are parts by weight, molecular weight is weight average molecular weight, temperature is in degrees Centigrade, and pressure is at or near atmospheric.

Example 1a. Impregnation of Porous Carrier with an Active Pharmaceutical Ingredient (APAP)

A set of experiments have been conducted successfully using a Glatt fluidized bed granulator. The model API used in those experiments was acetaminophen (APAP) and the porous carrier was anhydrous dibasic calcium phosphate ($CaHPO_4$). Among various solvents, methanol was chosen due to its relatively high vapor pressure, low surface tension on the carrier surface and good solubility of APAP in it. Three subsets of experiments were conducted with targeted high, medium and low drug loading. Hard gelatin capsules were then filled with the impregnated material using a CAP 8 filling machine by Capsugel. Filled capsules were tested for weight variability, content uniformity, and blend homogeneity. The same impregnated material was afterwards milled and filled in capsules again to assess the effect that milling has on blend uniformity. A summary of all results is given in Table 1. In some cases, it was observed that the larger particles of porous carrier contained slightly less API than the smaller particles. In such situations, the impregnated carrier was passed through a pin mill prior to filling it into capsules in order to erase the correlation between granule size and drug content and improve uniformity further.

TABLE 1

Blend and Content Uniformity in Capsules Filled with APAP impregnated $CaHPO_4$.

| % APAP Loading (wt API/wt pure $CaHPO_4$) | Blend Uniformity, % RSD | Capsule Total Weight Variability, % RSD | Drug Content Uniformity, % RSD |
| --- | --- | --- | --- |
| 8.82% (un-milled) | 1.05 | 2.00 | 1.73 |
| 8.82% (milled) | 0.54 | 1.19 | 1.65 |
| 1.02% (un-milled) | 0.70 | 1.52 | 1.18 |
| 1.02% (milled) | 0.56 | 1.73 | 1.91 |
| 0.1% (un-milled) | 0.99 | 0.79 | 1.01 |
| 0.1% (milled) | 0.42 | 2.25 | 2.79 |

Table 1 shows results obtained from the method for the formulation and manufacture of solid dosage forms by impregnation in fluidized bed. The technique generates blends with API RSD around 0.5%. Compressed tablets and/or filled capsules display RSD's<2% for drug content as low as 0.1% and as high as 10%, thus spanning most of the range of interest for poorly soluble highly potent compounds for oral delivery applications. The results show that the blend uniformity remains essentially unchanged as drug loading is decreased. Further, controlling the spray rate can yield highly uniform blends regardless of the API loading amount.

The ability to obtain low RSD's at low drug content is particularly important because low drug content products typically require lengthy development, usually resulting in complex, expensive, and unreliable manufacturing methods.

This method has the capability to achieve very uniform blends regardless of the drug loading. Upon milling, the blend uniformity is further increased, RSD is reduced by almost half. It should be noted that capsule filling was performed in a semi-automatic fashion resulting in some inconsistencies in the capsule's total weight variability, affecting in turn the drug content uniformity. All measurements, however, are well below the FDA's requirements.

Example 1b. Impregnation of Porous Carrier with an API (APAP)

A porous carrier was impregnated with acetaminophen (APAP) as with the method described in Example 1a. Table 2 shows the blend and content uniformity in tablets obtained from the method. In Table 2, the experiments for 9.91% APAP had particles less than 150 μm eliminated from the $CaHPO_4$ starting material. This was done in order to see if eliminating the fine particles of $CaHPO_4$ improved blend uniformity. The tablets were produced individually using a PRESSTER.

| % APAP Loading (wt API/wt pure $CaHPO_4$) | Blend Uniformity, % RSD | Total Weight Variability, % RSD | Drug Content Uniformity, % RSD |
| --- | --- | --- | --- |
| 11.69% (un-milled) | 1.92 | 1.07 | 2.57 |
| 11.69% (milled) | 0.28 | 1.75 | 1.79 |
| 9.91% (un-milled) | 2.02 | 1.35 | 3.17 |
| 9.91% (milled) | 0.46 | 1.84 | 1.71 |
| 8.82% (un-milled) | 0.67 | 0.69 | 1.24 |

The fluid bed (FB) method yields substantially uniform blends without any additives. The results show that milling significantly improves blend uniformity. FIG. 2A shows photomicrographs of the particular pharmaceutical excipient used—pure anhydrous $CaHPO_4$. FIG. 2B shows photomicrographs of different size fractions of $CaHPO_4$ impregnated with APAP. Additional properties and characteristics of the compositions and methods were analyzed.

Figure 3A:
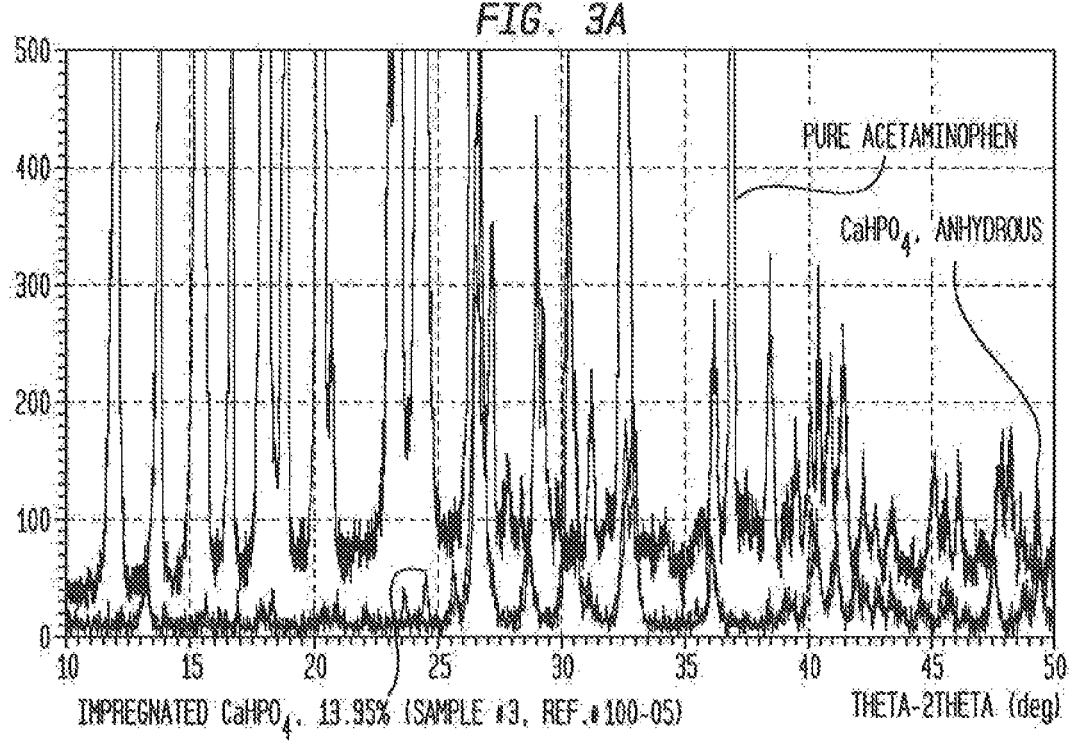
FIG. 3A shows comparison of XRD patterns for impregnated $CaHPO_4$ (11.69% loading), pure $CaHPO_4$, and pure acetaminophen (APAP).
Figure 3B:
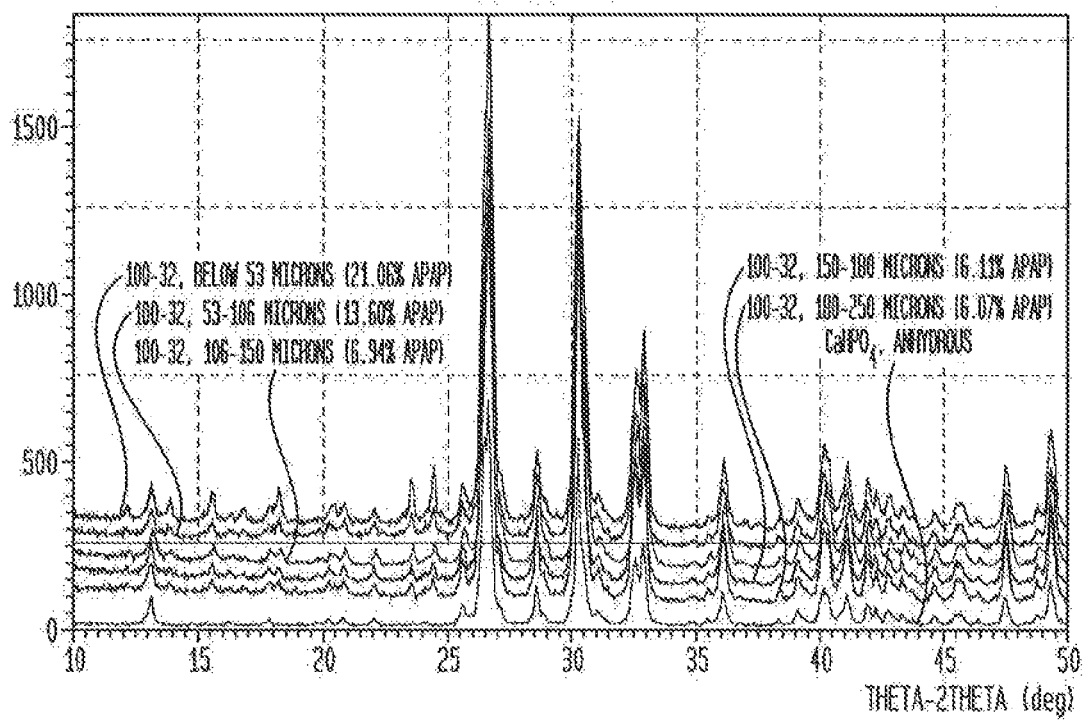
FIG. 3B which shows comparison of XRD patterns for various sieved fractions of impregnated $CaHPO_4$ (8.87% average loading).

FIG. 3A shows comparison of XRD patterns for impregnated $CaHPO_4$ (11.69% loading), pure $CaHPO_4$ and pure APAP. FIG. 3B shows comparison of XRD patterns for various sieved fractions of impregnated $CaHPO_4$ (8.87% average loading).

Figure 4B:
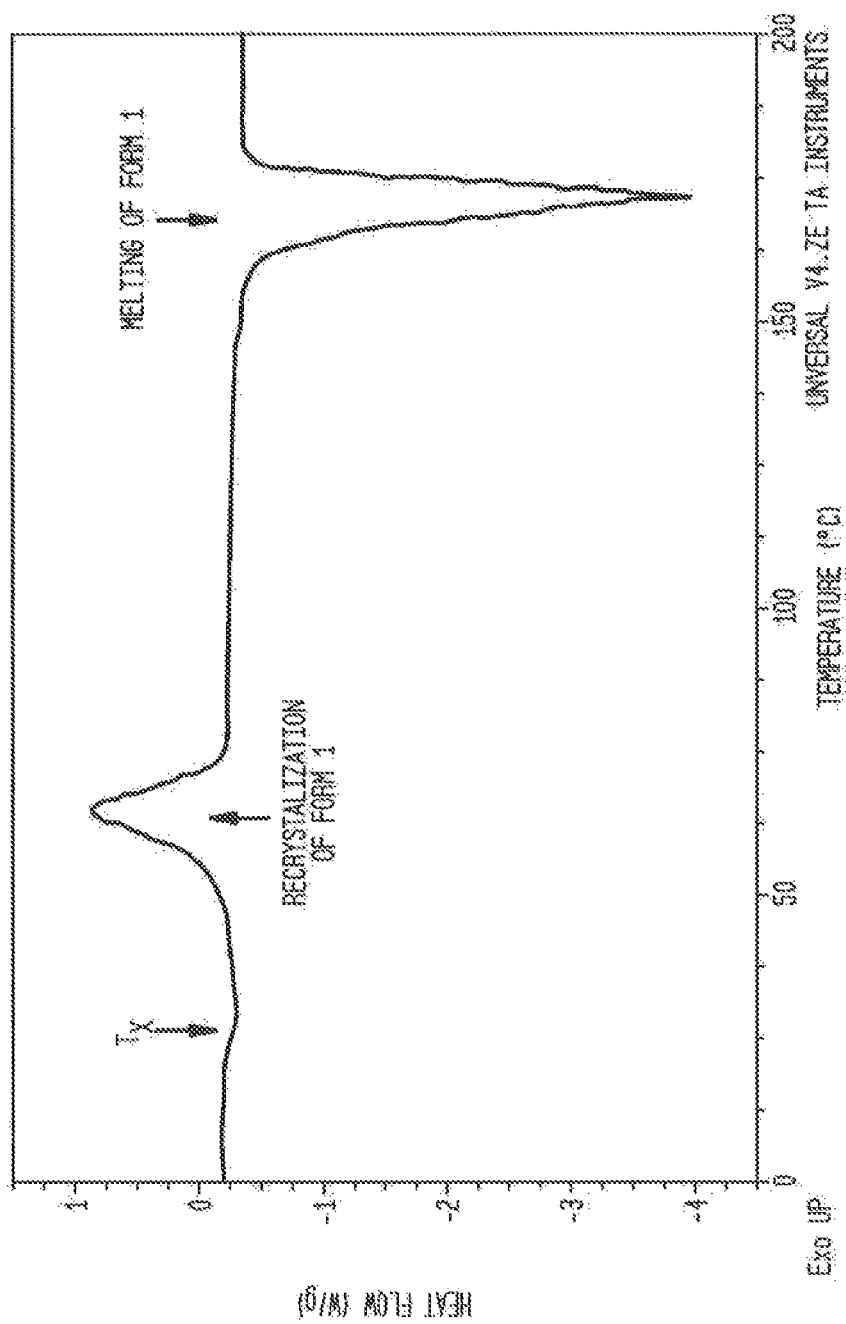
FIG. 4B shows the DSC profile for pure amorphous acetaminophen (APAP) (Sheng Q., Avale, P., Saklarvala, R., Craig, D., (2008). An Investigation into the effects of thermal history on the crystallization behavior of amorphous paracetamol, European Journal of Pharmaceutics and Biopharmaceutics, 69, 364-371).

FIG. 4A shows a graph of DSC analysis of various sieved fractions of impregnated $CaHPO_4$ (8.87% average loading). The DSC profile always exhibits broadening. Without being limited by theory, this may be due to molecular dispersions in the small pores. From the DSC analysis there is no evidence for amorphous content. FIG. 4B shows a typical DSC profile for pure and for amorphous APAP.

Figure 5:
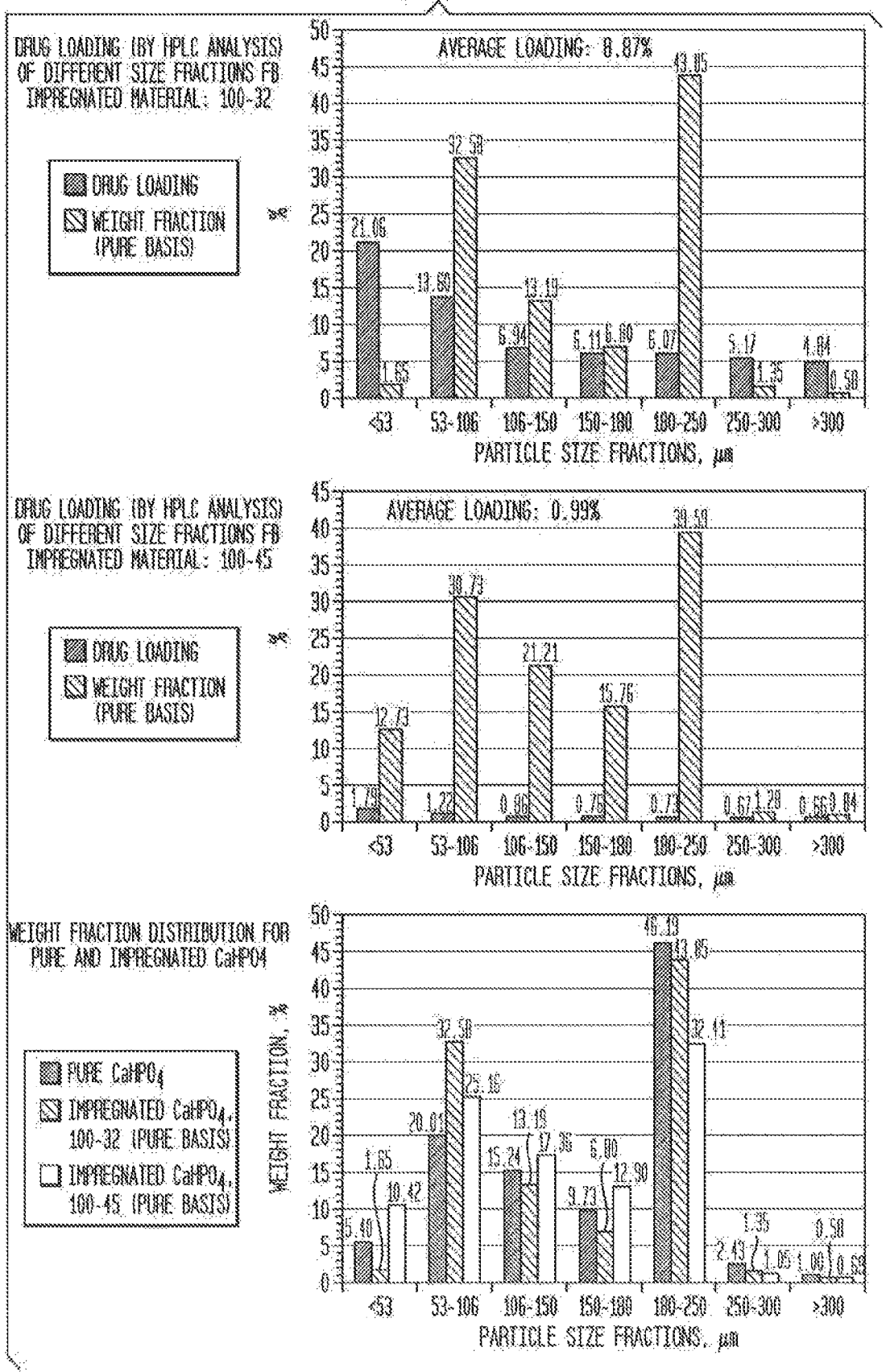
FIG. 5 shows graphs of weight fraction (%) and acetaminophen (APAP) loading (%) versus particle size fractions (μm) for impregnated $CaHPO_4$ (average loadings 8.87% and 0.99%) and pure $CaHPO_4$.

The drug loading and weight fraction at different size ranges for pure and impregnated $CaHPO_4$ also was analyzed (FIG. 5).

Figure 6:
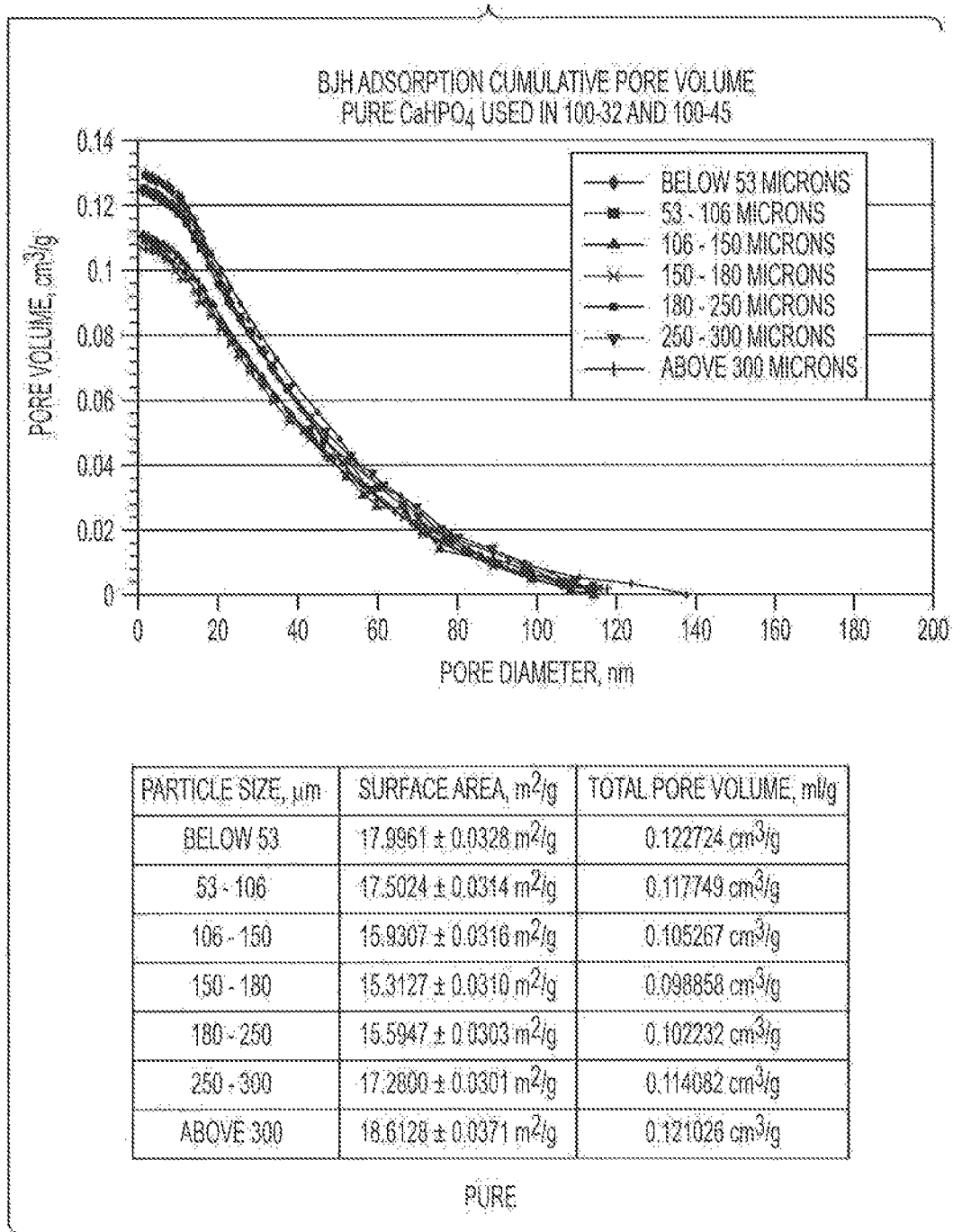
FIG. 6 shows graphs of cumulative pore size distributions (pore volume vs. pore size) and tables of total surface area ($m^2/g$) and total pore volume ($cm^3/g$) for various sieved fractions of pure and impregnated $CaHPO_4$ (high loading).
Figure 7:
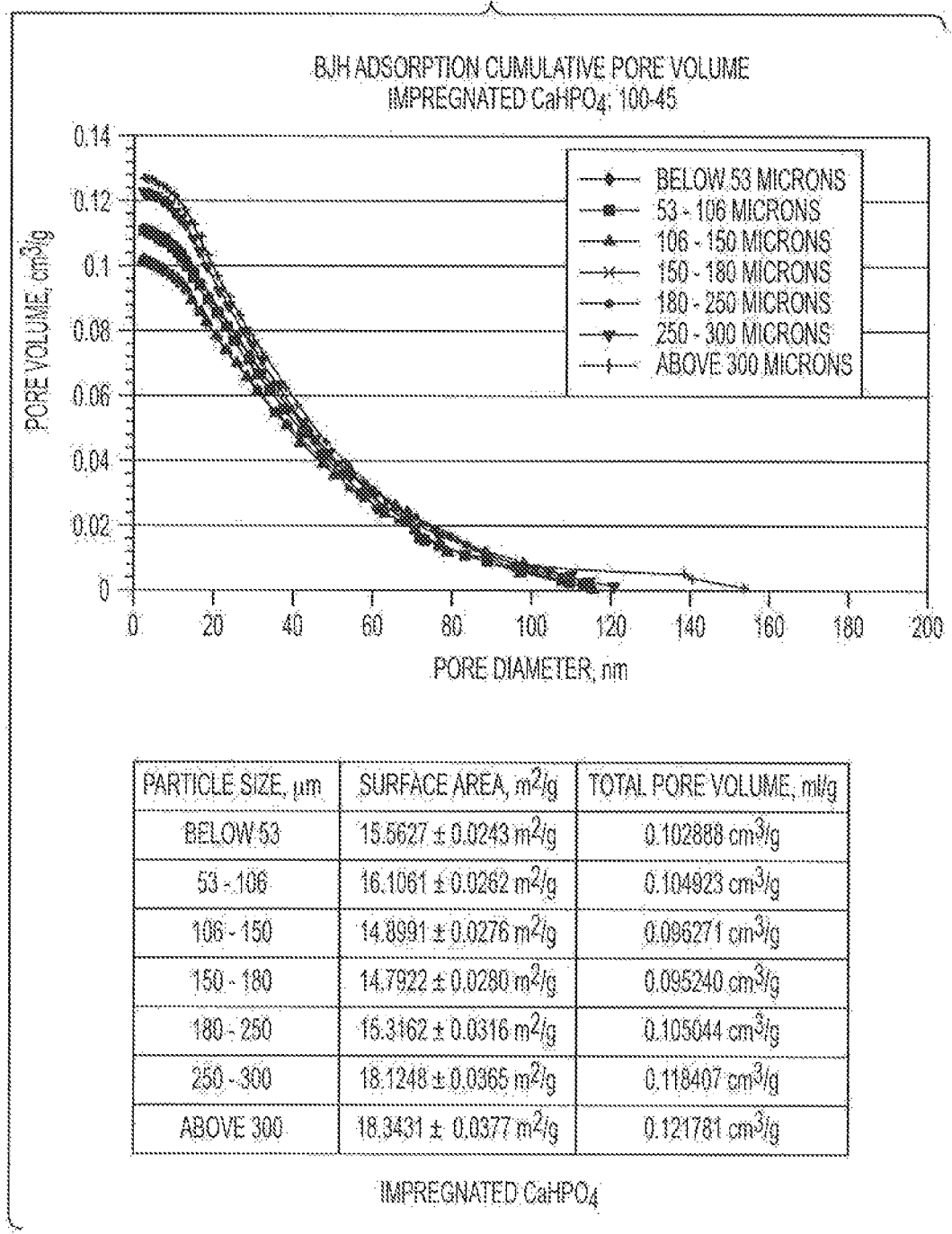
FIG. 7 shows graphs of cumulative pore size distributions (pore volume vs. pore size) and tables of total surface area ($m^2/g$) and total pore volume ($cm^3/g$) for various sieved fractions of pure and impregnated $CaHPO_4$ (low loading).
Figure 7:
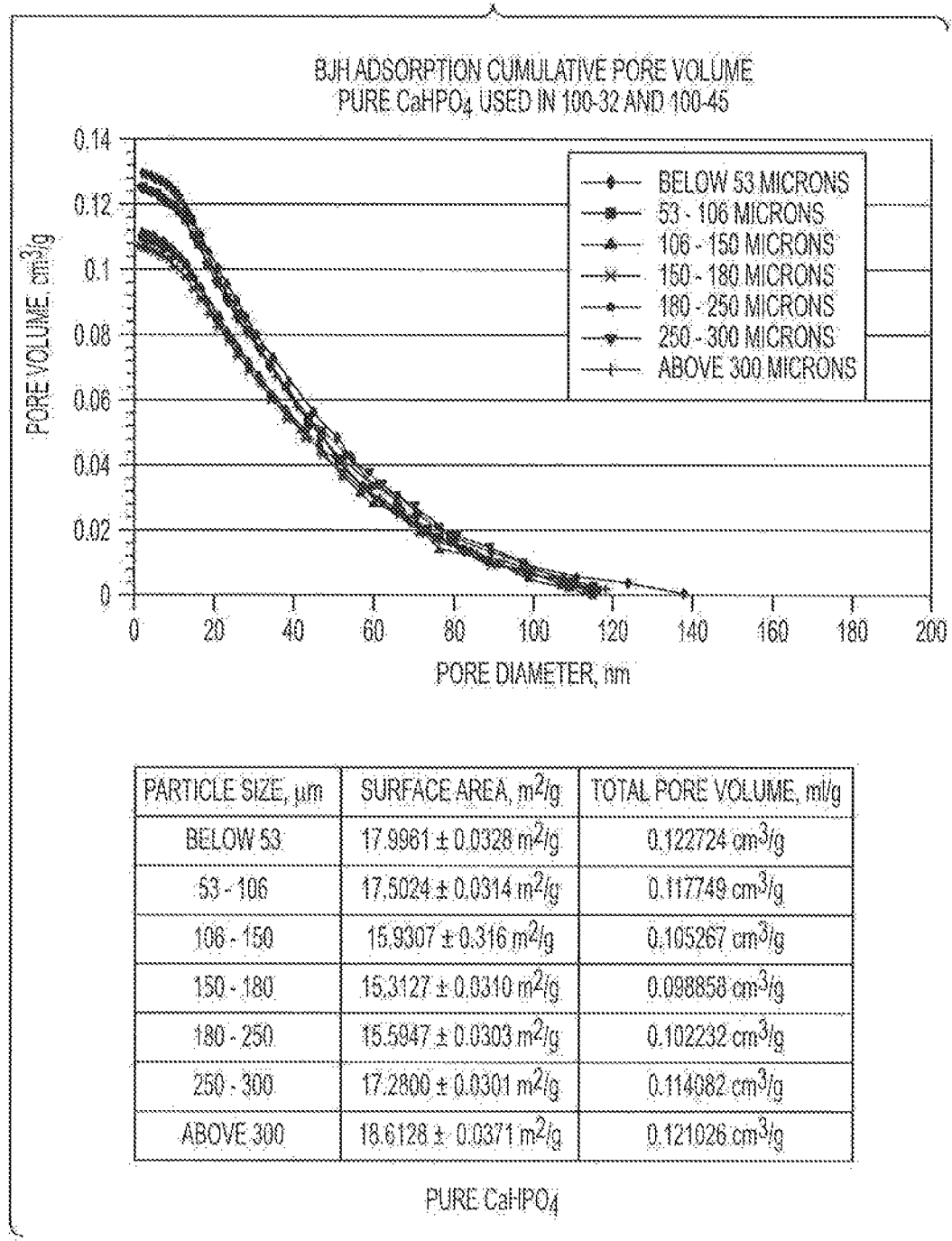

The specific surface area (SSA) and pore size distribution for various sieved fractions of impregnated $CaHPO_4$ with 8.8% loading (FIG. 6) and 1.0% loading (FIG. 7) was analyzed.

The dissolution profiles of capsules of different (%) loadings (1.0% and 8.8%) were analyzed (FIGS. 8A and 8B). The percentage of dissolved APAP in FIG. 8B, which shows data points over 100%, can be attributed to the following: (1) small errors in the calibration curve used; (2) small error in weighing of the capsules; (3) some moisture content in the blend due to uncontrolled storage conditions.

Particle Size Distribution (PSD) measurements were determined (FIGS. 9A and 9B).

Figure 10:
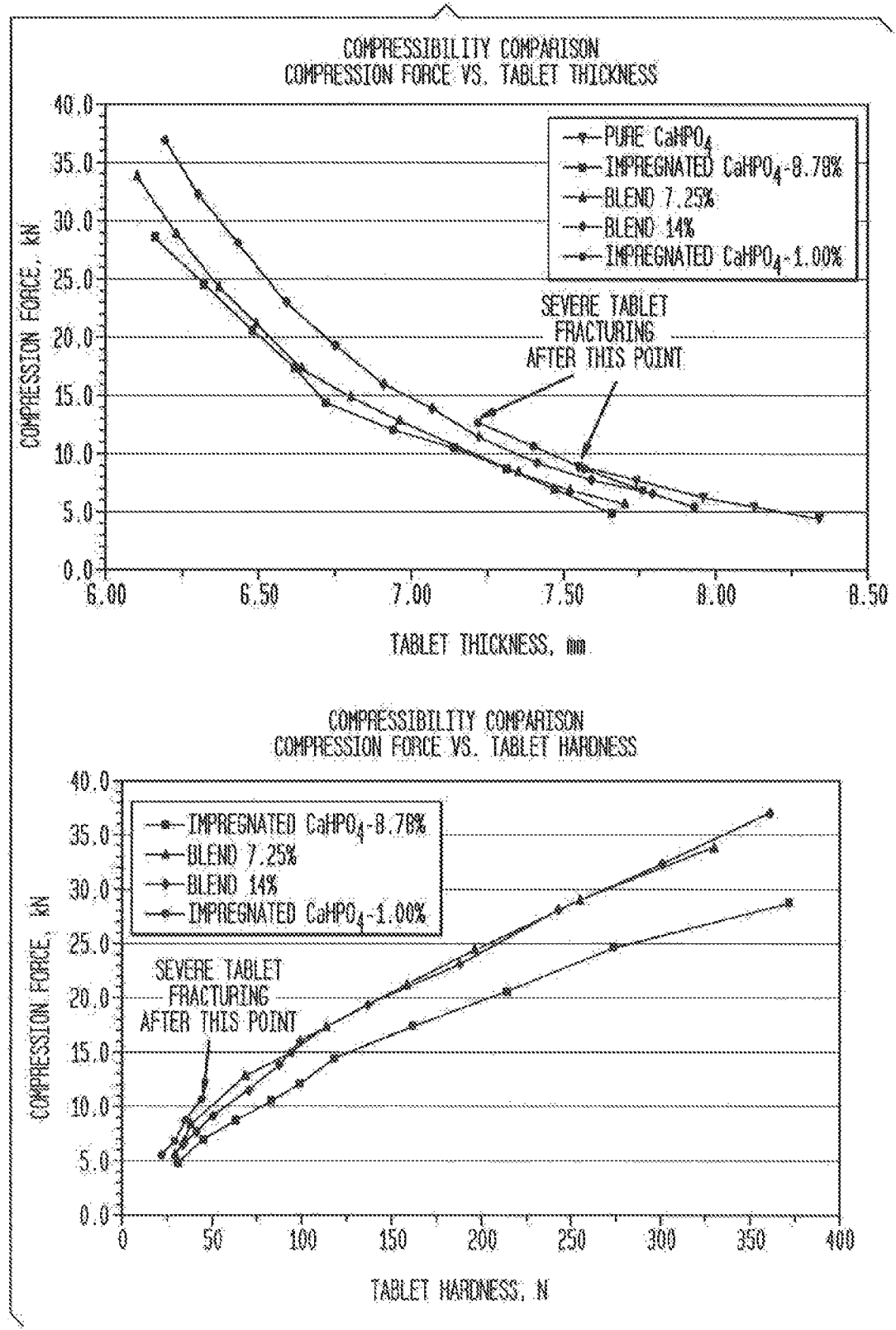
FIG. 10 (right panel) shows a graph of tablet thickness (mm) versus compression force (kN)

Compressibility experiments were performed using a PRESSTER MMC (FIG. 10). The results show that pure $CaHPO_4$ and $CaHPO_4$ impregnated with 1% APAP behave similarly. As the impregnated amount increases, for a given compression force tablet hardness increases and tablet thickness decreases; there is an overall increase in compressibility.

Figure 11:
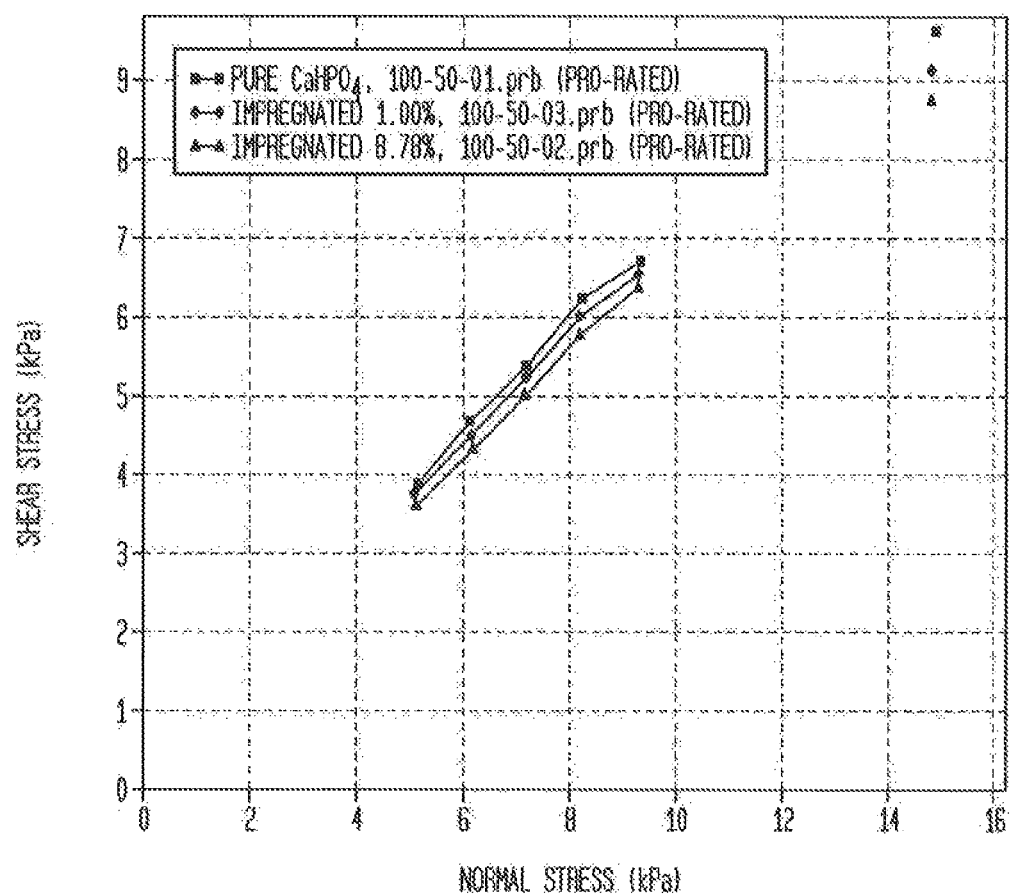
FIG. 11 shows a graph of shear cell measurements (normal stress, kPa versus shear stress, kPa, for pure and impregnated CaHPO$_4$ (high and low loadings).
Figure 12:
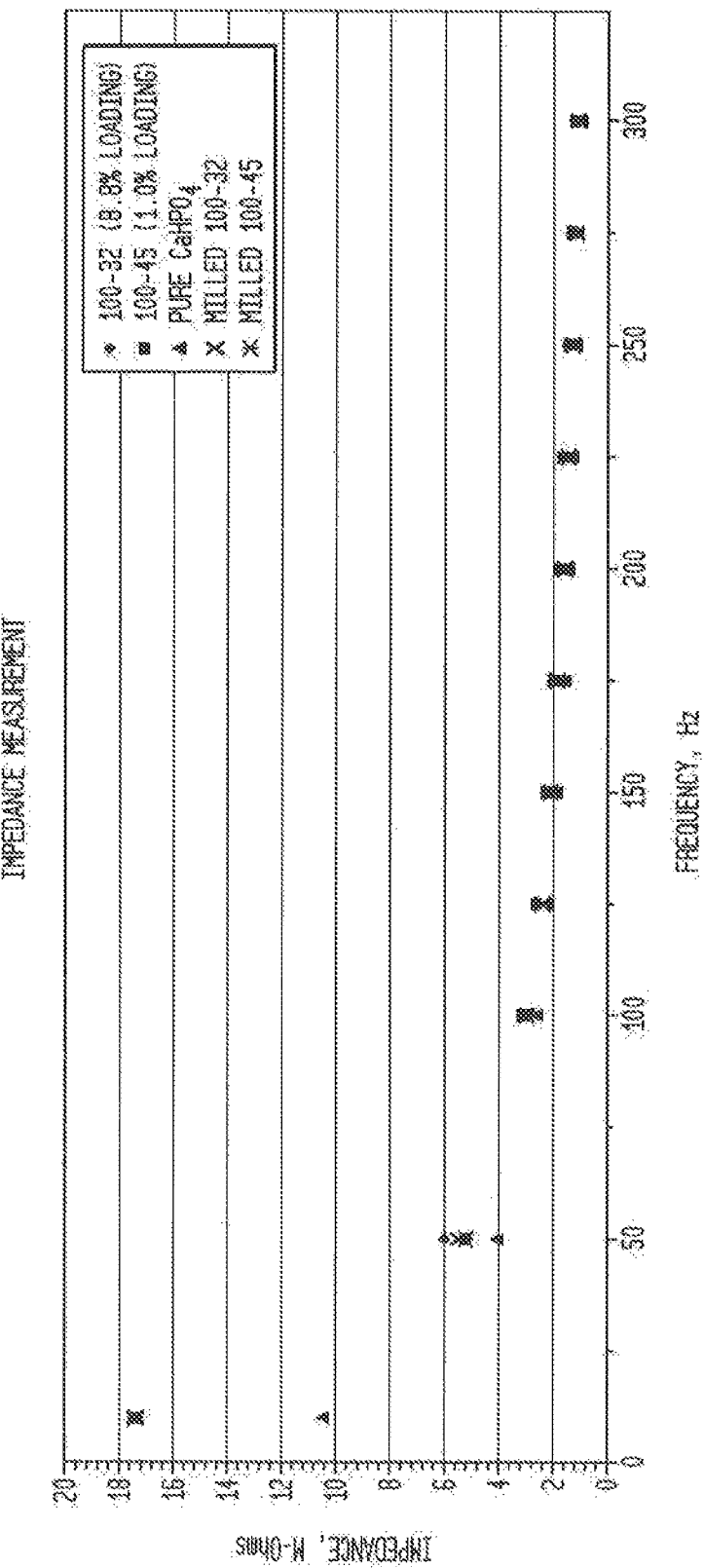
FIG. 12 shows a graph of impedance measurements (frequency, Hz, versus impedance, M-Ohms, for pure CaHPO$_4$, impregnated CaHPO$_4$ (high and low loadings) and milled impregnated CaHPO$_4$ (high and low loadings).

Shear Cell by FT4 was investigated (FIG. 11) as well as electrostatic properties (impedance) (FIG. 12).

Figure 13:
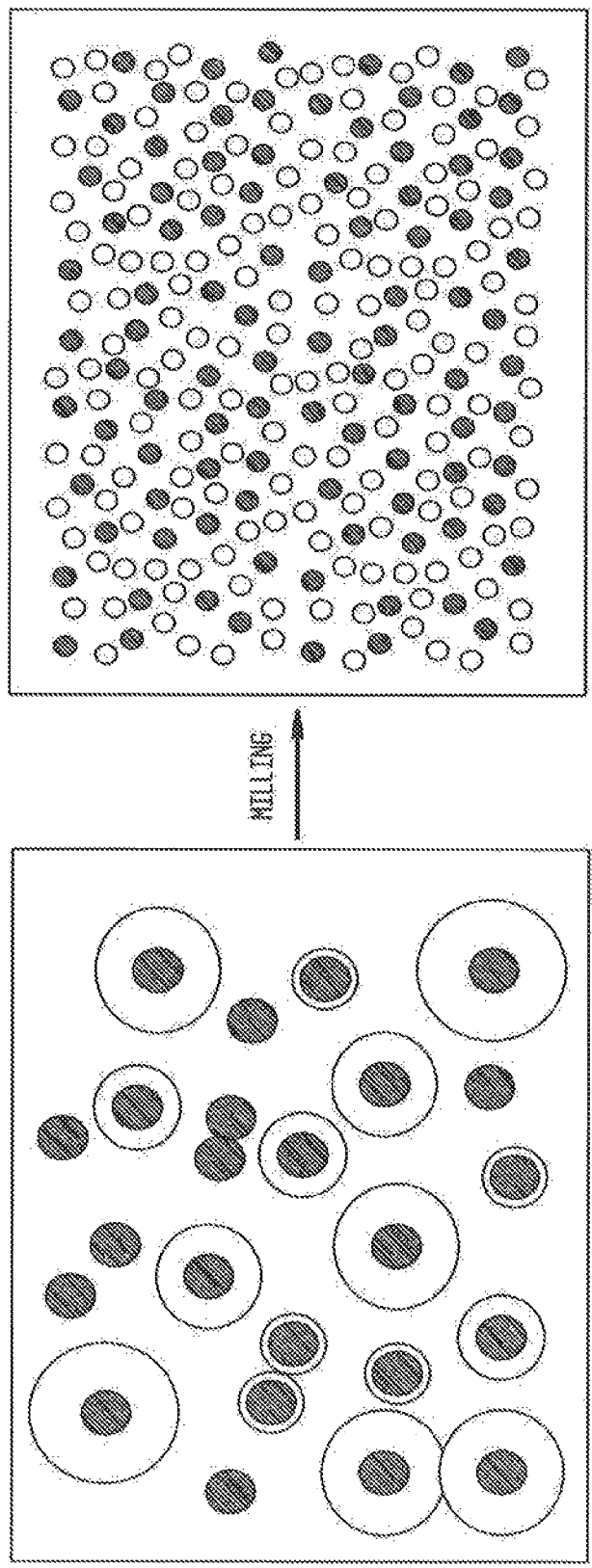
FIG. 13 shows an illustrative representation of the effect of milling on the blend uniformity.

FIG. 13 shows an illustrative representation of the effect of milling upon the blend.

These results show that the method has the capability to achieve very high uniformity blends regardless of the drug loading.

Example 2. Impregnation of Porous Carrier with an API (Ibuprofen)

A porous carrier was impregnated with Ibuprofen as with the methods described in Example 1. The results of blend uniformity of impregnated $CaHPO_4$ with Ibuprofen shown in FIG. 14 indicates that the manufacturing method of the described invention is not limited to only acetaminophen (APAP) but can be used for any other drug. The average loading shown in FIG. 14 (as determined by HPLC analysis) is slightly higher than the target loading. This is due to the fact that there is some loss of excipient (primarily very small fines) during the impregnation run, particularly through the bag filter of the fluidized bed. Such phenomenon will not be seen on large scale fluidized beds with properly sized filter bags.

FIG. 15 (DSC scans of various size fractions of impregnated $CaHPO_4$ with Ibuprofen) also shows an absence of amorphous content (upward peaks) and broadening of the melting peaks of Ibuprofen, and shifting to lower melting points (pure Ibuprofen melts at 77.3° C.). This is due to confinement-induced melting point depression effect, which is well known in the art, and indicates that the drug is impregnated in small pores.

FIG. 16 shows a dissolution profile of gelatin capsules filled with $CaHPO_4$ impregnated with Ibuprofen at 10% loading.

Example 3. Impregnation of Porous Carrier with an API (Indometacin/Indomethacin)

A porous carrier is impregnated with Indometacin (or Indomethacin) as with the methods described in Example 1.

Example 4. Impregnation of Porous Carrier with an API (Flufenamic Acid)

A porous carrier is impregnated with flufenamic acid as with the methods described in Example 1.

Example 5. Impregnation of Porous Carrier with an API (Imatinib)

A porous carrier is impregnated with Imatinib with the methods described in Example 1.

Example 6. Impregnation of Porous Carrier with an API (Erlotinib Hydrochloride)

A porous carrier is impregnated with erlotinib hydrochloride as with the methods described in Example 1.

Example 7. Impregnation of Porous Carrier with an API (Vitamin D)

A porous carrier is impregnated with vitamin D as with the methods described in Example 1.

Example 8. Impregnation of Porous Carrier with an API (Steroid)

A porous carrier is impregnated with a steroid as with the methods described in Example 1.

Example 9. Impregnation of Porous Carrier with an API (Estrodial)

A porous carrier is impregnated with estrodial as with the methods described in Example 1.

Example 10. Impregnation of Porous Carrier with an API (Therapeutic Agent)

A porous carrier is impregnated with a therapeutic agent as with the methods described in Example 1.

While the present invention has been described with reference to the specific embodiments thereof, it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. An impregnated porous carrier material made by a process comprising the steps of:
   (a) dissolving at least one active pharmaceutical ingredient (API) in a solvent to form an API solution;
   (b) spraying, by means not including spray drying, the at least one API solution of (a) into a bed of a preformed porous carrier in at least one of a fluidized bed, a stirred vessel and a tumbler in which the spray rate (in 1/second) equals mass of the API sprayed divided by a total of spray time (in seconds) multiplied by mass of the carrier (in kilograms) such that the spray rate is less than $0.5s^{-1}$, thereby forming at least one API impregnated porous carrier; and
   (c) drying the at least one API impregnated porous carrier, wherein the resulting at least one API impregnated porous carrier is suitable for producing an immediate release finished drug product such that any single API content variability in the finished drug product has a relative standard deviation of less than 3%.

2. The impregnated porous carrier material of claim 1, wherein the at least one active pharmaceutical ingredient (API) comprises acetaminophen, ibuprofen, indometacin/indomethacin, flufenamic acid, imatinib, flufenamic acid, erlotinib hydrochloride, vitamin D, a steroid, estrodial, or a combination thereof.

3. The impregnated porous carrier material of claim 1, wherein the porous carrier has a porosity of 20% to 80% pores by volume.

4. The impregnated porous carrier material of claim 1, wherein the porous carrier has a specific surface area of at least 6 $m^2/g$.

5. The impregnated porous carrier material of claim 1, wherein the porous carrier is a pharmaceutically acceptable material.

6. The impregnated porous carrier material of claim 1, wherein the porous carrier comprises $CaHPO_4$.

7. The impregnated porous carrier material of claim 1, wherein the solvent is an inorganic or organic solvent selected from water, ethanol, methanol, isopropyl alcohol (IPA), acetone, 1-propanol, 1-pentanol, acetonitrile, butanol, methyl ethyl ketone (MEK), methyl acetate, 2-methyl tetrahydrofuran, isopropyl acetate (IPAc), n-hexane, ethyl acetate (EtOAc), n-heptane, an aqueous solvent and supercritical $CO_2$.

8. The impregnated porous carrier material of claim 1, wherein the at least one API is sprayed in a fluid bed processor or in an agitated vessel.

9. The impregnated porous carrier material of claim 1, wherein the impregnated carrier is dried in a fluid bed processor, an agitated vessel or an oven.

10. The impregnated porous carrier material of claim 1, where the dried impregnated porous carrier is milled.

11. An immediate release pharmaceutical dosage form comprising the impregnated porous carrier material of claim 1.

12. The immediate release pharmaceutical dosage form of claim 11 further comprising at least one of a filler, a compaction binder, a lubricant, and a disintegrant.

13. The immediate release pharmaceutical dosage form of claim 11, further comprising an additional API.

14. The immediate release pharmaceutical dosage form of claim 11, wherein an amount of the at least one API is 0.01% to 10% by weight of the dosage form.

15. The immediate release pharmaceutical dosage form of claim 11, wherein an amount of the at least one API is 10% to 40% by weight of the dosage form.

16. The immediate release pharmaceutical dosage form of claim 11, wherein an amount of the at least one API is greater than 0.1% by weight of the dosage form.

17. The immediate release pharmaceutical dosage form of claim 11, wherein the dosage form is at least one of a tablet, a capsule, and an inhalable product.

18. A sustained release pharmaceutical dosage form comprising the impregnated porous carrier material of claim 1.

19. A solid oral pharmaceutical dosage form comprising the impregnated porous carrier material of claim 1.

* * * * *